(12) United States Patent
Kim et al.

(10) Patent No.: US 10,139,428 B2
(45) Date of Patent: Nov. 27, 2018

(54) PHASE CORRECTION DEVICE, ACTION IDENTIFICATION DEVICE, ACTION IDENTIFICATION SYSTEM, MICROCONTROLLER, PHASE CORRECTION METHOD, AND PROGRAM

(71) Applicant: Renesas Electronics Corporation, Tokyo (JP)

(72) Inventors: Kichung Kim, Tokyo (JP); Masaharu Matsudaira, Tokyo (JP)

(73) Assignee: RENESAS ELECTRONICS CORPORATION, Tokyo (JP)

(*) Notice: Subject to any disclaimer, the term of this patent is extended or adjusted under 35 U.S.C. 154(b) by 230 days.

(21) Appl. No.: 14/942,122

(22) Filed: Nov. 16, 2015

(65) Prior Publication Data

US 2016/0139175 A1    May 19, 2016

(30) Foreign Application Priority Data

Nov. 17, 2014 (JP) ................. 2014-232807
Dec. 26, 2014 (JP) ................. 2014-264297
Aug. 5, 2015 (JP) ................. 2015-154753

(51) Int. Cl.
| | |
|---|---|
| *G01P 21/00* | (2006.01) |
| *G01P 15/18* | (2013.01) |
| *A61B 5/11* | (2006.01) |
| *G01C 9/00* | (2006.01) |

(52) U.S. Cl.
CPC ............ *G01P 21/00* (2013.01); *A61B 5/11* (2013.01); *G01C 9/00* (2013.01); *G01P 15/18* (2013.01); *A61B 2562/0219* (2013.01)

(58) Field of Classification Search
CPC . G01P 21/00; G01P 15/18; A61B 5/11; A61B 5/112; A61B 5/1123; A61B 2562/0219
See application file for complete search history.

(56) References Cited

U.S. PATENT DOCUMENTS

2010/0318257 A1* 12/2010 Kalinadhabhotla ..... G01P 21/00
701/31.4
2013/0110010 A1    5/2013 Fuke et al.

FOREIGN PATENT DOCUMENTS

| JP | H 10-267651 A | 10/1998 |
|---|---|---|
| JP | 2011-217928 A | 11/2011 |
| JP | 2013-094316 A | 5/2013 |

* cited by examiner

*Primary Examiner* — Paul West
(74) *Attorney, Agent, or Firm* — McGinn I.P. Law Group, PLLC.

(57) ABSTRACT

There are included a standard deviation calculation unit that receives a plurality of acceleration data and calculates a standard deviation of the plurality of acceleration data for each specified time period, an average calculation unit that receives the plurality of acceleration data and calculates an average value of the acceleration data for each specified time period, a phase estimation unit that estimates a phase of the average value in a space having a first coordinate axis and a second coordinate axis by using the average value when the standard deviation is smaller than a specified threshold, and a phase correction unit that performs phase correction of the average value by using the estimated phase.

20 Claims, 26 Drawing Sheets

| | X | Y | Z |
|---|---|---|---|
| ACTUALLY ACQUIRED ACCELERATION DATA | $a_{X0}$ | $a_{Y0}$ | $a_{Z0}$ |
| CORRECTED ACCELERATION DATA | $a'_{X0}$ | $a'_{Y0}$ | $a'_{Z0}$ |
| AVERAGE OF CORRECTED ACCELERATION DATA | $M(a'_{X0})$ | $M(a'_{Y0})$ | $M(a'_{Z0})$ |
| AVERAGE ACCELERATION | $a_X$ | $a_Y$ | $a_Z$ |
| AVERAGE OF AVERAGE ACCELERATION | $M(a_X)$ | $M(a_Y)$ | $M(a_Z)$ |
| IDEAL AVERAGE ACCELERATION | $a_{XI}$ | $a_{YI}$ | $a_{ZI}$ |
| AVERAGE OF IDEAL AVERAGE ACCELERATION | $M(a_{XI})$ | $M(a_{YI})$ | $M(a_{ZI})$ |

Fig. 15

PHASE CORRECTION DEVICE, ACTION IDENTIFICATION DEVICE, ACTION IDENTIFICATION SYSTEM, MICROCONTROLLER, PHASE CORRECTION METHOD, AND PROGRAM

CROSS-REFERENCE TO RELATED APPLICATIONS

This application is based upon and claims the benefit of priority from Japanese patent applications No. 2014-232807 filed on Nov. 17, 2014, No. 2014-264297 filed on Dec. 26, 2014, and No. 2015-154753 filed on Aug. 5, 2015, the disclosure of which is incorporated herein in its entirety by reference.

BACKGROUND

The present invention relates to a measurement device, a phase correction device, an action identification device, an action identification system, a microcontroller, a phase correction method, and a program.

Various devices that measure the amount of activity of people using an acceleration sensor and systems that identify the action of people based on the measurement results have been proposed. Further, such devices and systems are applied also to measurement of the amount of activity and identification of the action of animals other than people.

Japanese Unexamined Patent Application Publication No. 2011-217928 discloses a system that mounts an acceleration sensor to an animal, converts acceleration data acquired from the acceleration sensor into an angle, and estimates the state of the animal from the angle and kinetic momentum. According to this technique, the acceleration sensor that detects the accelerations in three axes (x-axis, y-axis and z-axis) that are orthogonal to one another is fixed to a harness that is worn around an animal's body or a collar. When fixing the acceleration sensor, the x-axis, the y-axis and the z-axis are set to coincide with the front-back direction, the left-right direction and the up-down direction of an animal, respectively. Then, a measurement device calculates a front-back tilt angle $\theta x$ and a left-right tilt angle $\theta y$ of the x-y plane with respect to the z-direction based on the acceleration data detected by the acceleration sensor and displays a change in those tilt angles two-dimensionally. The measurement device further performs short-time Fourier transform on synthetic acceleration obtained by synthesizing the three-axis acceleration data. It is thereby possible to decompose the synthetic acceleration into frequency components and calculate a frequency distribution. The measurement device identifies the action of the animal based on the frequency distribution.

Japanese Unexamined Patent Application Publication No. H10-267651 discloses a method for correcting the displacement between the axis of an acceleration sensor mounted on an object under test and the axis of the object under test when they do not match. Specifically, a regular hexahedron housing on which an acceleration sensor is mounted is brought into contact with an object under test to measure the acceleration of gravity in the state of rest. This procedure is performed on every side of the hexahedron.

The action identification by an acceleration sensor applied also to people. Japanese Unexamined Patent Application Publication No. 2013-094316 discloses a method for estimating the walking state of people in a short time. According to this technique, an acceleration sensor is worn near the waist of a target person to detect the acceleration in the horizontal direction (left-right direction) that is substantially orthogonal to the moving direction of the person. Then, the variation of autocorrelation of acceleration data during walking is used as a feature quantity, and the walking state is estimated using SVM (Support Vector Machine).

SUMMARY

However, according to the description of the configuration disclosed in Japanese Unexamined Patent Application Publication No. 2011-217928, the acceleration sensor is mounted on an animal with the axis of the acceleration sensor and the gravity direction coinciding with each other. However, it is difficult to accurately achieve this. Specifically, when an animal moves, the position on which the acceleration sensor is mounted and the axial direction change. Then, the standard value of the acceleration differs in each measurement, which makes it difficult to accurately estimate the state of the animal from the acceleration data.

The configuration disclosed in Japanese Unexamined Patent Application Publication No. H10-267651 has a problem that it is difficult to produce the resting state for calibration with the acceleration sensor mounted on an animal. Further, because it discloses a method for correcting the displacement between axes in the early stage when the acceleration sensor is mounted on an object under test, when the axial direction varies with time such as when the acceleration sensor is mounted on an animal, the acceleration data is acquired without correcting the displacement between axes. Then, in the case of correcting the displacement occurring between axes as needed, the act of manually controlling the acceleration sensor or the like is required, such as measuring the acceleration several times as changing the position of the side of the hexahedron of the housing.

Further, both of Japanese Unexamined Patent Application Publications Nos. 2011-217928 and 2013-094316 perform the action identification based on the assumption that the acceleration sensor is placed in a desired position and direction, and the position and direction of the acceleration sensor that have been determined once are maintained. However, in reality, even for the same object, it is extremely difficult to always place the acceleration sensor in a fixed position and direction. If the placement position and direction of the acceleration sensor are different each time, phase displacement occurs in the acceleration data obtained each time.

Further, there is a case where the acceleration sensor is gradually displaced from the initial placement position and direction due to the motion of an object. In this case also, phase displacement occurs in the acceleration data with the lapse of time.

The action identification using an acceleration sensor requires a procedure to determine a threshold and machine learning parameter based on acceleration data. If the displacement of the placement position and direction of the acceleration sensor does not occur, the same threshold or parameter can be applied every time to the same object no matter how many times the placement of the acceleration sensor and the acquisition of the acceleration data are performed. However, as described above, in the case where a phase difference in acceleration data occurs in each measurement, it is necessary to calculate a threshold and parameter for each measurement. In other words, it is difficult to use a common threshold and parameter for a plurality of measurements. Further, it takes a lot of time and work to calculate a threshold and parameter for each measurement, which is inefficient.

One solution to the above problem is to perform calibration when placing an acceleration sensor at an object and thereby correct a phase difference. However, it is necessary to maintain the resting state during calibration. If the object is an animal, it is difficult to maintain the resting state for a certain period of time. Further, this method cannot correct a phase difference that occurs due to the motion of an object after placement or the like.

The present invention has been accomplished to solve the above problems and an object of the present invention is thus to provide a phase correction device, an action identification device, an action identification system, a microcontroller, a phase correction method and a program capable of making appropriate correction.

The other problems and novel features of the present invention will become apparent from the description of the specification and the accompanying drawings.

According to one embodiment, a phase correction device includes a standard deviation calculation unit that receives a plurality of acceleration data and calculates a standard deviation of the plurality of acceleration data for each specified time period, a representative value calculation unit that receives the plurality of acceleration data and calculates a representative value of the acceleration data for each specified time period, a phase estimation unit that estimates a phase of the representative value in a space having a first coordinate axis and a second coordinate axis by using the representative value when the standard deviation is smaller than a specified threshold, and a phase correction unit that performs phase correction of the representative value by using the estimated phase.

According to one embodiment, an action identification device includes the above-described phase correction device, an identification learning unit that performs machine learning by using the representative value after phase correction by the phase correction device, and an identification processing unit that performs action identification by using the representative value after phase correction by the phase correction device.

According to one embodiment, an action identification system includes the above-described action identification device, and a transmitting unit including an acceleration sensor that is mounted on an object and outputs the acceleration data.

According to one embodiment, a microcontroller includes the above-described action identification device, and a resistor setting unit that sets any one of the identification learning unit and the identification processing unit to an operating state according to external control.

According to one embodiment, a phase correction method includes a standard deviation calculation step of receiving a plurality of acceleration data and calculating a standard deviation of the plurality of acceleration data for each specified time period, a representative value calculation step of receiving the plurality of acceleration data and calculating a representative value of the acceleration data for each specified time period, a phase estimation step of estimating a phase of the representative value in a space having a first coordinate axis and a second coordinate axis by using the representative value when the standard deviation is smaller than a specified threshold, and a phase correction step of performing phase correction of the representative value by using the estimated phase.

One embodiment is a program for causing a computer to execute the phase correction described above.

According to the present invention, it is possible to provide a measurement device, a measurement system, a measurement method and a program capable of correcting a mounting error of an acceleration sensor by using statistical information of acceleration data even after the acceleration sensor is mounted on an object under test.

BRIEF DESCRIPTION OF THE DRAWINGS

The above and other aspects, advantages and features will be more apparent from the following description of certain embodiments taken in conjunction with the accompanying drawings, in which:

FIG. 15 is a list of variables used in the description of embodiments of the present invention.

DETAILED DESCRIPTION

Specific embodiments of the present invention are described hereinafter in detail with reference to the drawings.

First Embodiment

Figure 1:
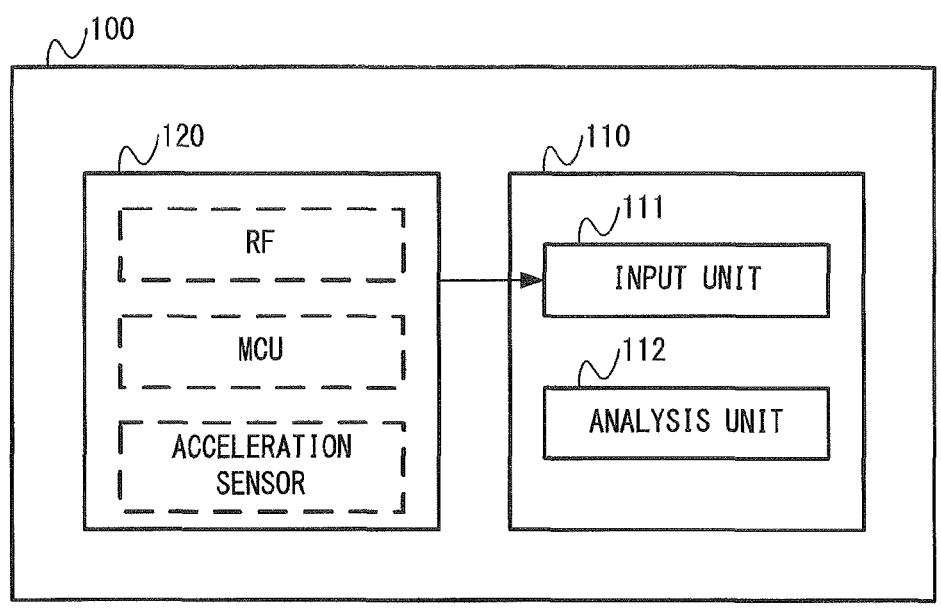
FIG. 1 is a view showing the configuration of a measurement system 100 according to a first embodiment.

The configuration of a measurement system 100 according to a first embodiment of the present invention is described first with reference to FIG. 1.

The measurement system 100 includes a measurement device 110 and a sensor module 120.

The sensor module 120 is used by being mounted on an object under test, and measures the acceleration generated by the motion of the object under test and outputs acceleration data indicating a measured value. The sensor module 120 typically includes an acceleration sensor, an MCU (Micro Control Unit) that generates acceleration data from an output signal of the acceleration sensor and outputs it, and an RF unit that modulates the acceleration data and transmits it by wireless way. Instead of the RF unit, the sensor module 120 may include various communication interfaces for transmitting acceleration data by wired way. It is assumed that the acceleration sensor is capable of outputting the three-axis (x, y and z) acceleration.

The measurement device 110 receives the acceleration data output from the sensor module 120, performs statistical processing on the acceleration data and thereby modifies a mounting error of the acceleration sensor. The measurement device 110 is typically an information processing device such as a PC (personal computer) or a server computer, and it is implemented by a CPU (Central Processing Unit), a storage device such as a volatile or nonvolatile memory, an input/output device and the like. The measurement device 110 performs specified processing based on a program stored in the storage device and thereby logically implements an input unit 111 and an analysis unit 112, which are described later.

The input unit 111 receives the acceleration data from the sensor module 120. The acceleration data is received by reception and demodulation of a radio signal using an access point or by wired communication using communication interfaces, for example.

The analysis unit 112 performs statistical processing on the acceleration data acquired by the input unit 111 and modifies a mounting error of the acceleration sensor.

The overview of the way of modifying a mounting error of the acceleration sensor by using the measurement system 100 according to the first embodiment is described next. The case where an object under test is an animal and the sensor module 120 is mounted on the animal to acquire acceleration data is described hereinafter as an example.

First, the sensor module 120 is mounted on an animal. The sensor module 120 is preferably mounted on a position in the axial direction where acceleration data can be easily translated later and at which the motion or acceleration is likely to occur. In this embodiment, the sensor module 120 is mounted on an animal's head. Further, the sensor module 120 is mounted so that, among the three axes (x, y and z) which the sensor module 120 can measure, the x-direction coincides with the moving direction of the animal, the y-direction coincides with the left-right direction of the animal, and the z-direction coincides with the up-down direction of the animal.

Next, acceleration data is acquired by letting the animal act freely for a given period of time such as 10 minutes, for example. The sensor module 120 transmits the acceleration data generated by the acceleration sensor by wireless or wired to the measurement device 110.

The measurement device 110 receives the acceleration data and performs the following processing. First, the analysis unit 112 of the measurement device 110 calculates the average value of the acceleration data for each certain time period. For example, in the case of acquiring the acceleration data at a sampling rate of 400 Hz and calculating the average value every one second, the average value of 400 pieces of acceleration data during one second is obtained. This average value is referred to hereinafter as the average acceleration. The analysis unit 112 performs the calculation of the average acceleration for each of the three directions (x, y and z).

Then, the analysis unit 112 compares the statistical distribution of actually acquired acceleration data and the statistical distribution of predetermined ideal acceleration data and corrects the actually acquired acceleration data. The concept of this processing is described hereinbelow.

Figure 2:
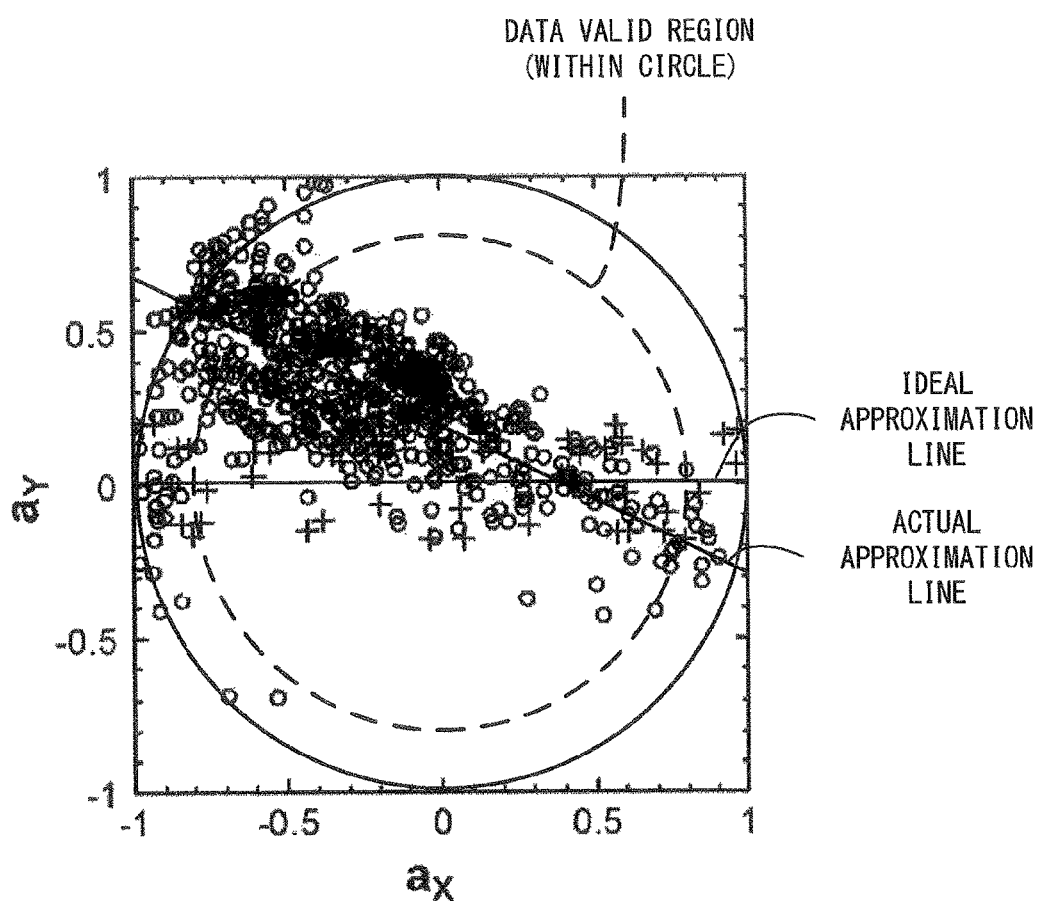
FIG. 2 is a view showing the concept of correction processing according to the first embodiment.

FIG. 2 is a graph in which the average accelerations in the x-direction and the y-direction calculated from the actually acquired acceleration data are plotted with circle marks "o". On the other hand, plus marks "+" indicate the predetermined ideal average acceleration in the x-direction and the y-direction.

Generally, when the average accelerations are plotted, the distribution with a certain pattern is obtained according to the posture or action of an animal. In this example, because the acceleration sensor is mounted so that the y-direction coincides with the left-right direction of an animal, ideally, the average accelerations are distributed along the line $a_y=0$ of acceleration in the y-direction according to the symmetrical motion of the animal ("+" distribution). In other words, the distribution of ideal average accelerations should approximate to the line $a_y=0$.

However, in reality, the left-right direction of an animal and the y-axis do not coincide due to a mounting error of the acceleration sensor. Further, due to a reason such as a change in the mounting position caused by the motion of an animal, the ideal axis predetermined and the actual axis of the acceleration sensor are deviated from each other. Accordingly, the distribution of actual average accelerations (the distribution of "o") is deviated from the distribution of ideal average accelerations (the distribution of "+"). Specifically, the approximation line of the distribution of actual average accelerations is slightly tilted relative to the approximation line of the distribution of ideal average accelerations.

The analysis unit 112 calculates the slope of the approximation line of average accelerations in the x-direction and the y-direction by the least squares method, for example. At this time, a data region to be read may be specified in order to improve the accuracy. The calculated slope indicates the displacement between the ideal axis and the actual axis. For example, the analysis unit 112 corrects the acceleration data by a correction coefficient that is calculated based on the calculated slope.

Note that, although the correction coefficient is calculated based on the statistical distribution of average accelerations in the two directions x and y in this embodiment, the distribution in another given axis direction may be used if the ideal statistical distribution can be predetermined. Further, it is not limited to the two directions, and the correction coefficient may be calculated in the same manner using the statistical distribution in the three-dimensional space where the three axes x, y and z are plotted.

Further, in the above-described process, it is not always necessary for the analysis unit 112 to generate a graph where the distribution of actual average accelerations (the distribution of "o") and the distribution of ideal average accelerations (the distribution of "+") are plotted in practice. The analysis unit 112 needs to perform only the calculation of a correction coefficient based on the displacement of the statistical distribution on the background of the concept as described above. However, it is preferred that the analysis unit 112 carries out the generation and display of the above-described graph in order to present it to a user, for example.

Figure 3:
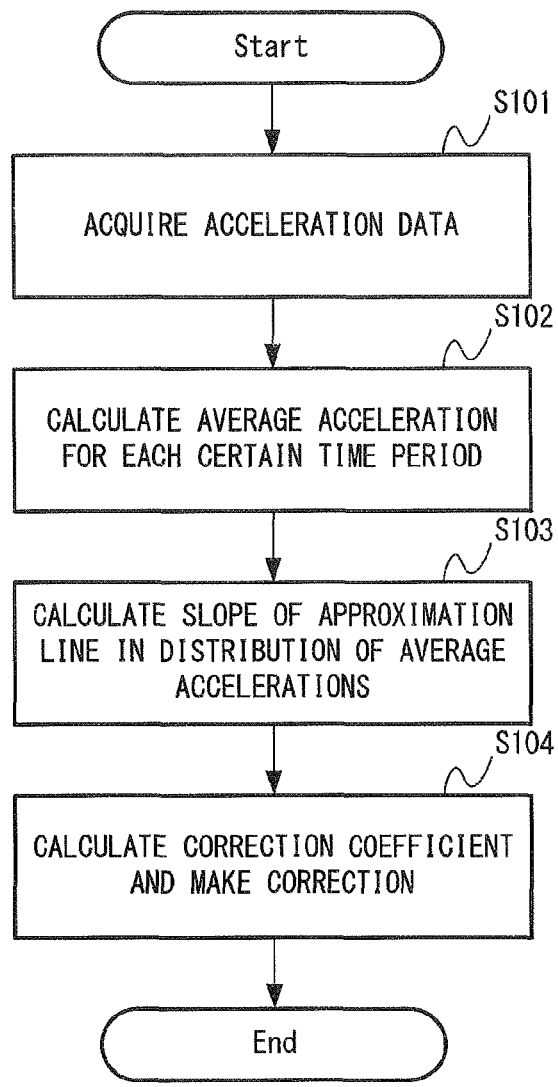
FIG. 3 is a flowchart showing the operation of the measurement system 100 according to the first embodiment.

Specific processing for the correction of acceleration data described above which is performed by the analysis unit 112 is described hereinafter in detail with reference to the flowchart of FIG. 3.

S101: Acquire Acceleration Data

The input unit 111 of the measurement device 110 receives acceleration data that is transmitted from the sensor module 120 by wireless or wired communication. The input unit 111 can end the acquisition of acceleration data when a predetermined measurement time has passed.

S102: Calculate Average Acceleration Per Unit Time

The analysis unit 112 calculates the average value of accelerations for each certain time period based on the acceleration data that is acquired by the input unit 111. For example, in the case of calculating the average value every one second, the analysis unit 112 divides the whole acceleration data into groups of every one second and calculates the average value for each group. The analysis unit 112 performs the same processing for all of the three directions (x, y and z) where the acceleration sensor outputs the acceleration data.

S103: Calculate Slope of Approximation Line of Distribution of Average Accelerations The analysis unit 112 calculates a slope A of a straight line that approximates to the average accelerations calculated in S102. For example, the slope A of the approximation line on the x-y plane can be calculated by the following equation (1)

Equation 1

$$A = \frac{\Sigma_i(a_X(i) - M(a_X))(a_Y(i) - M(a_Y))}{\Sigma_i(a_X(i) - M(a_X))^2} \quad (1)$$

In the above equation, $a_X(i)$ is the value of the x-component of the i-th average acceleration, $M(a_X)$ is the average value of x-components of all average accelerations, $a_Y(i)$ is the value of the y-component of the i-th average acceleration, and $M(a_Y)$ is the average value of y-components of all average acceleration.

Note that the analysis unit 112 may perform the linear approximation in S103 by using only some of average accelerations, not all of average accelerations calculated in S102. For example, a data valid region that excludes average accelerations that are distributed near the circular arc with a radius of 1 shown in FIG. 2 is set, and the above-described linear approximation is performed using only the average accelerations inside this data valid region. It is thereby possible to perform linear approximation efficiently. Such a data valid region can be defined by a condition expression such as $x^2+y^2<(0.8)^2$, for example.

S104: Calculate and Correct Correction Coefficient

The analysis unit 112 calculates a correction coefficient using the slope A of the approximation line that is calculated in S103 and corrects the acceleration data. In this embodiment, the analysis unit 112 corrects the acceleration data by the following equations (2) and (3).

$$a'_{X0} = a_{X0}\cos(\tan^{-1}A) + a_{Y0}\sin(\tan^{-1}A) \quad (2)$$

$$a'_{Y0} = -a_{X0}\sin(\tan^{-1}A) + a_{Y0}\cos(\tan^{-1}A) \quad (3)$$

In the above equations, $a'_{X0}$ and $a'_{Y0}$ are the x-component and y-component of the corrected acceleration data, $a_{X0}$ and $a_{Y0}$ are the x-component and y-component of the acceleration data (acquired in S101) before correction, and $\cos(\tan^{-1} A)$ and $\sin(\tan^{-1} A)$ are correction coefficients. FIG. 15 shows a list of variables that are used in the equation for correction described above or another equation for correction described later.

By the processing in S104, the acceleration data is corrected so that the slope of the approximation line of actual average accelerations calculated in S103 matches the ideal slope of the approximation line of average accelerations. Consequently, the displacement of a mounting axis of the acceleration sensor that occurs due to a mounting error or the lapse of time is substantially corrected.

Note that, although the case of performing the calculation of the slope of the approximation line, the calculation of correction coefficients and the correction by using the equations (1) to (3) is described in this embodiment, this embodiment is not limited thereto. The analysis unit 112 may correct the acceleration data by other suitable equations or the like as long as the function of correcting the axis of the distribution of average accelerations is implemented.

Further, although the acceleration data is corrected in S104 in this embodiment, the average acceleration may be corrected, for example, depending on purpose.

Further, in this embodiment, the average acceleration is calculated in S102 and the correction coefficient is calculated using the average acceleration. However, this embodiment is not limited thereto, and the correction coefficient may be calculated using a given representative value other than the average value or using actually acquired acceleration data as it is, for example, instead of using the average acceleration. Note that, however, randomness of data distribution is suppressed and appropriate results are likely to be obtained in the case of using a representative value such as the average value compared with the case of using actually acquired acceleration data as it is. Another advantage is that a user can easily understand an operation in the process of specifying a data valid region, checking a graph and the like.

In this embodiment, the measurement device 110 corrects actual acceleration data by using a correction coefficient based on a difference between the distribution of average accelerations of the actually acquired acceleration data for each certain time period and the distribution of ideal average accelerations. The measurement device 110 can thereby perform correction (calibration) of acceleration data by using only the statistical information of the acceleration data. Therefore, after mounting the acceleration sensor on a person, an animal or the like as an object under test, even when the person or the animal is in motion, it is possible to correct a mounting error of the acceleration sensor without direct operation of the acceleration sensor. Further, it is possible to continuously correct the displacement of the axis that occurs with the lapse of time.

Second Embodiment

A second embodiment has a feature that it ends the acquisition of acceleration data in the case where it is determined that a sufficient amount of data for performing statistical processing is obtained in the acceleration data acquisition step (S101 in the first embodiment).

Specifically, while the first embodiment performs calibration of the acceleration sensor using statistical data, the second embodiment examines whether the statistical data is valid or not in advance.

The configuration of the measurement system 100 according to the second embodiment is substantially the same as that of the first embodiment and thus not redundantly described.

Figure 4:
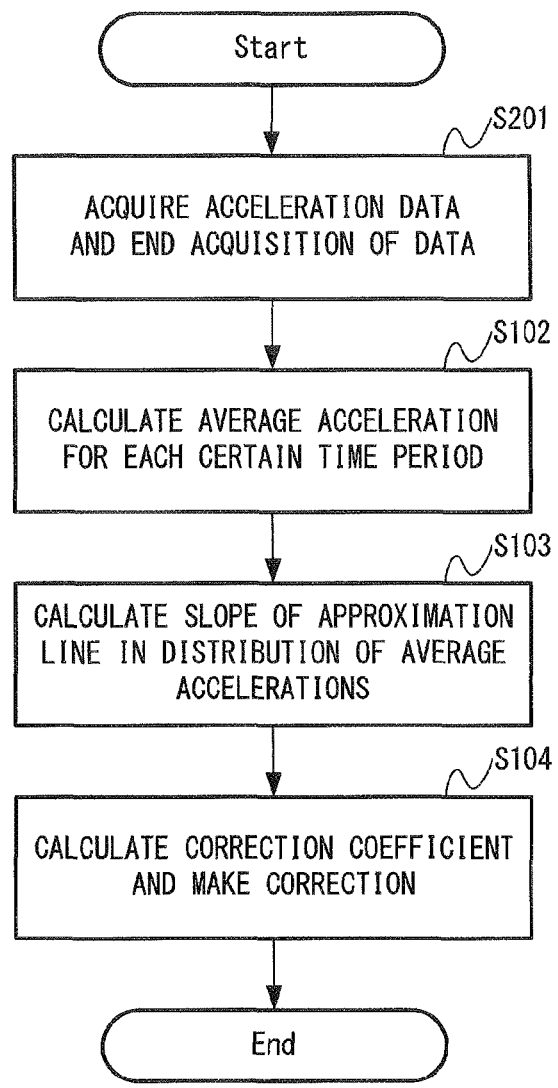
FIG. 4 is a flowchart showing the operation of a measurement system 100 according to a second embodiment.

The correction of acceleration data which is performed by the measurement device 110 according to the second embodiment is described hereinafter with reference to the flowchart of FIG. 4. Only the processing that is different from the first embodiment is mainly described below.

S201: Acquire Acceleration Data and End Acquisition of Data

The input unit 111 of the measurement device 110 receives acceleration data that is transmitted from the sensor module 120 by wireless or wired communication in the same manner as in S101 according to the first embodiment.

The input unit 111 calculates a coefficient of determination as needed for the acquired acceleration data, and ends the acquisition of acceleration data at the point of time when the variation of the coefficient of determination becomes equal to or less than a specified value. The coefficient of determination is the statistic indicating the linearity of data. The coefficient of determination is a statistical measure, which is a value from 0 to 1, and it is closer to 1 as the distribution of target data is closer to a straight line.

Figure 5:
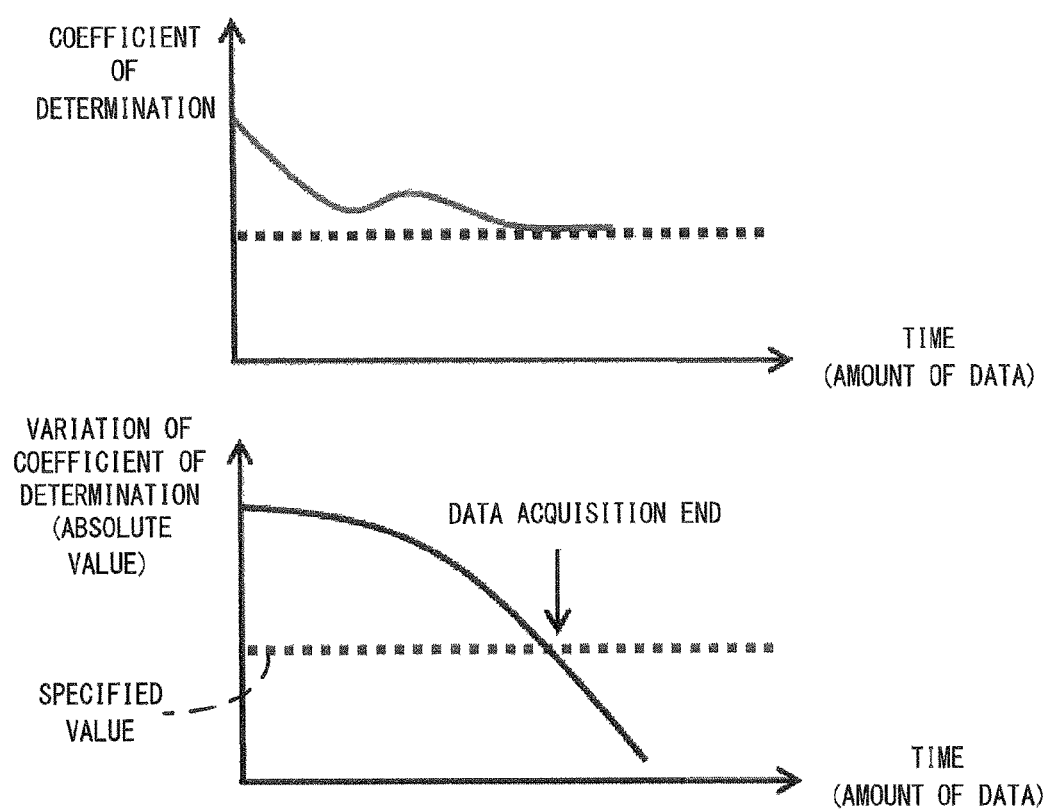
FIG. 5 is a view showing the operation of the measurement system 100 according to the second embodiment.

The coefficient of determination has characteristics that it has a large value when the amount of data is small and gradually converts to a certain value as the amount of data increases in the process of accumulating data. Therefore, the input unit 111 observes the variation (absolute value) of the coefficient of determination as needed and, when the variation falls below a specified value (for example, 0.001), for example, it is possible to determine that sufficient points of measurement (acceleration data) can be obtained (FIG. 5).

Note that it is more preferred to perform the above-described determination by using not the coefficient of determination but the variation in the coefficient of determination. This is because the coefficient of determination largely varies depending on noise (abnormal value) and the amount of data, and an error can occur when the above-described determination is performed using the coefficient of determination. On the other hand, because the variation in the coefficient of determination converges as the amount of data increases, it is suitable for use in the determination.

The equation (4) for calculating the coefficient of determination and the equation (5) for calculating the variation in the coefficient of determination are as follows.

$$R^2 = 1 - \frac{\Sigma_i(a_Y(i) - Aa_X(i))^2}{\Sigma_i(a_Y(i) - M(a_Y))^2} \cdot \frac{N-1}{N-2} \quad (4)$$

$$dR^2 = |R^2(n) - R^2(n-1)| \quad (5)$$

In the above equations, $R^2$ is the coefficient of determination, N is the number of all data, and n is the number of determinations of the coefficient of determination.

Note that, although the case of determining the timing to end the acquisition of data based on the coefficient of determination or the variation in the coefficient of determination is described in this embodiment, this embodiment is not limited thereto. The input unit 111 may determine whether the amount of acquired data is sufficient for statistical processing by another appropriate indicator.

When it is determined that a sufficient amount of acceleration data is acquired, the input unit 111 transmits a signal for stopping or suspending the acquisition or transmission of acceleration data to the sensor module 120 by wireless or wired communication. Alternatively, the input unit 111 may simply stop or suspend the acquisition of acceleration data.

S102 to S104:

The analysis unit 112 performs the correction of acceleration data in the same procedure as in the first embodiment by using the acceleration data acquired in S201.

In this embodiment, when the input unit 111 determines that a sufficient amount of data for performing statistical processing is obtained, it stops the acquisition of acceleration data. Thus, because the acquisition of data is stopped or suspended when a sufficient amount of data for statistical processing is obtained, the data acquisition work can be automated. For example, it is feasible to end the processing in a shorter time than the specified time in the first embodiment when a sufficient amount of data is acquired or perform the measurement for a longer time than the specified time when the amount of data is not sufficient. Further, in the case where the system is equipped with a battery as a power supply of the sensor module 120, it is possible to suppress the consumption of the battery by measuring acceleration data efficiently in this embodiment.

Third Embodiment

Although the example of correcting the displacement of the axis of the acceleration sensor is shown in the first embodiment, the third embodiment has a feature that it further corrects the displacement of acceleration values.

Figure 6:
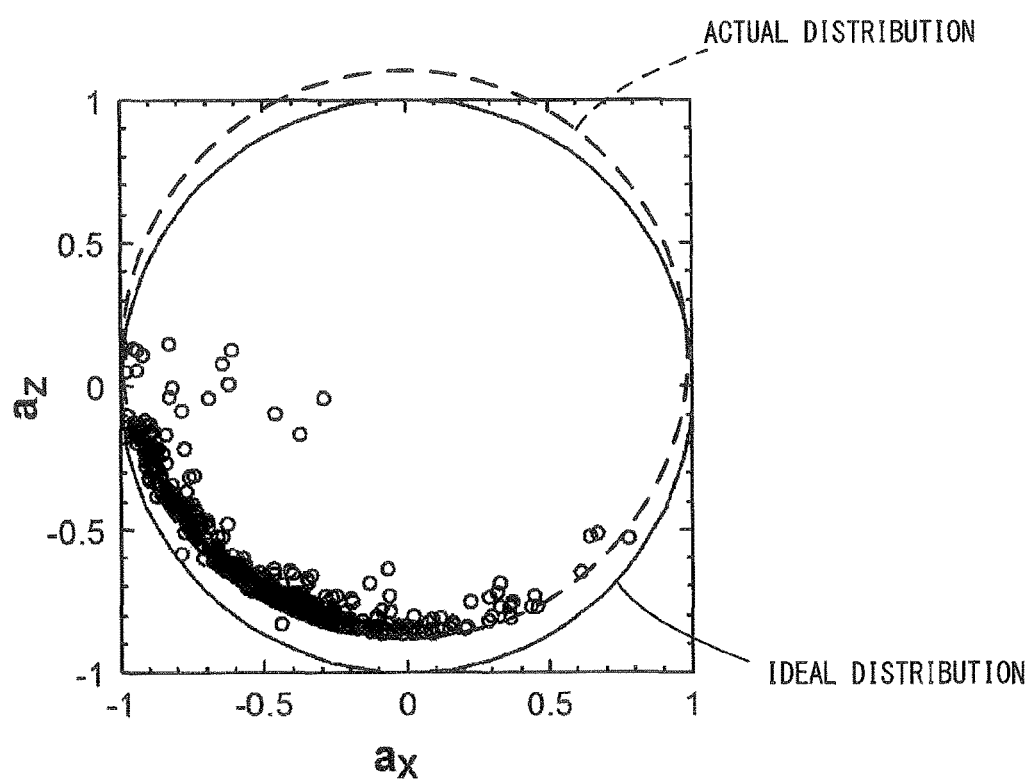
FIG. 6 is a view showing the concept of correction processing according to a third embodiment.

In the case where an object under test on which an acceleration sensor is mounted operates without any deviation, the average value of accelerations output from the acceleration sensor should be a value close to the acceleration of gravity (1 G). However, this cannot be achieved in some cases due to reasons such as the initial position when starting up the acceleration sensor, an individual difference in the acceleration sensor and the like. For example, the average accelerations per second in the x-direction and the z-direction are plotted as shown in FIG. 6, it is ideal that the average accelerations are distributed along the circular arc which is indicated by the solid line. On the other hand, in some cases, the distribution of the actually acquired average accelerations is the circular arc which is indicated by the dotted line, which is shifted in the z-direction from the ideal distribution.

Figure 7:
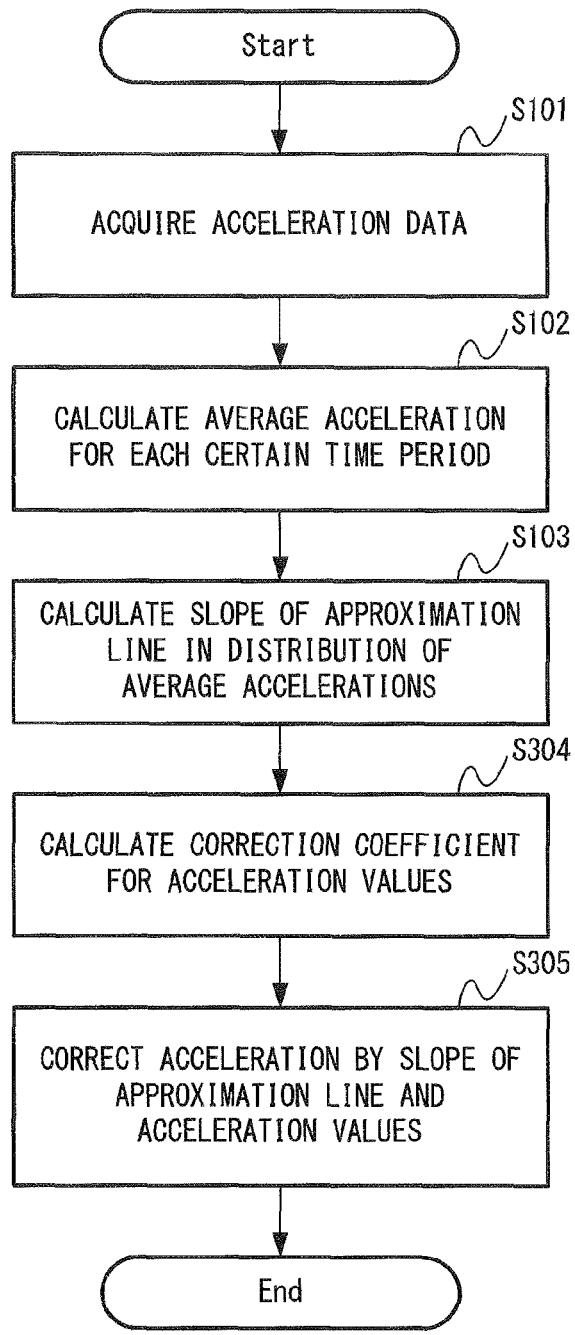
FIG. 7 is a flowchart showing the operation of a measurement system 100 according to the third embodiment.

To avoid this, in this embodiment, a correction value C for correcting the displacement of the distribution shown in FIG. 7 is calculated, and the actual acceleration data is corrected using the correction value so that the actual distribution matches the ideal distribution. Stated differently, while the rotation of axis of the distribution is corrected in the first embodiment, the displacement (shift error) of the origin of the distribution is corrected in the third embodiment.

The configuration of the measurement system 100 according to the third embodiment is substantially the same as that of the first embodiment and thus not redundantly described.

The correction of acceleration data which is performed by the measurement device 110 according to the third embodiment is described hereinafter with reference to the flowchart of FIG. 7. Only the processing that is different from the first embodiment is mainly described below.

S101 to S103:

The input unit 111 of the measurement device 110 acquires acceleration data from the sensor module 120. The analysis unit 112 calculates the average value of accelerations for each certain time period for the acquired acceleration data. Further, the analysis unit 112 calculates the slope A of the line that approximates the distribution of the average accelerations.

S304: Calculate Correction Coefficient for Acceleration Values

The analysis unit 112 calculates a correction coefficient C for correcting acceleration values by the following equation (6).

$$C = \text{mean}(a_Z - \sqrt{1-a_X^2}) \quad (6)$$

In the above equation, $a_X$ and $a_Z$ are the x-component and the z-component of the actually acquired average acceleration. Note that, the correction coefficient C may be calculated using the x-component and the z-component of the average acceleration corrected using the slope A of the approximation line in S305, which is described later, instead of $a_X$ and $a_Z$.

S305: Correct Acceleration by Correction Coefficient Based on Slope of Approximation Line and Acceleration Values The analysis unit 112 corrects the acceleration data by the correction coefficient using the slope A of the approximation line (equations (2) and (3)). After that, the calculated correction coefficient C is added to the z-component of the acceleration data to thereby correct the acceleration data. For example, in the data set plotted in FIG. 6, the correction value C is calculated as −0.119. In this case, −0.119 is added to the z-component of the acceleration data, and thereby the distribution of the average accelerations along the dotted line is shifted to the distribution along the ideal solid line.

Note that, in this embodiment, the configuration that corrects the displacement of acceleration values is described as the one that complements the configuration that corrects the displacement of the axis of the acceleration sensor according to the first embodiment. However, the configuration according to the third embodiment may be implemented independent of the first embodiment. Specifically, the processing that corrects the displacement of acceleration values by the correction value C for the acceleration values may be performed without performing the processing that corrects the displacement of the axis by the correction coefficient using the slope A of the approximation line.

Further, although the example that calculates the correction value C by the equation (6) and makes correction is described in this embodiment, this embodiment is not limited thereto. The analysis unit 112 may correct the acceleration data by another appropriate expression or the like as long as the function of correcting the center of the distribution of average accelerations is implemented.

Further, although the acceleration data is corrected in this embodiment, the average acceleration may be corrected, for example, depending on purpose.

Further, although the correction coefficient is calculated using the average acceleration in this embodiment, the correction coefficient may be calculated using a given representative value other than the average value or using actually acquired acceleration data as it is, for example, instead of using the average acceleration.

In this embodiment, the measurement device 110 performs the processing of correcting the displacement of acceleration values. It is thereby possible to correct an error of acceleration data due to the initial position when starting up the sensor, an individual difference in the device and the like even after the sensor module 120 is mounted on an object under test such as an animal.

Fourth Embodiment

A fourth embodiment has a feature that the accuracy of correction is improved by taking the type of action of an object under test (for example, a person or animal) into consideration as well in the correction of acceleration data described in the first embodiment. In general, it is considered that the distribution of acceleration data differs by action pattern (such as standing up, walking etc.). Thus, it is possible to improve the accuracy of correction by performing appropriate correction processing independently for each action pattern.

Further, although the first embodiment is based on the assumption that the distribution of average accelerations can be approximated by the straight line, the fourth embodiment proposes a technique of correction using the displacement of the center of gravity of acceleration data which is applicable also to the distribution of average accelerations where linear approximation is not appropriate.

In the measurement system 100 according to the fourth embodiment, the measurement device 110 needs to include an input device such as a keyboard, for example, to receive a user input. The other configuration is the same as that of the first embodiment.

Figure 8:
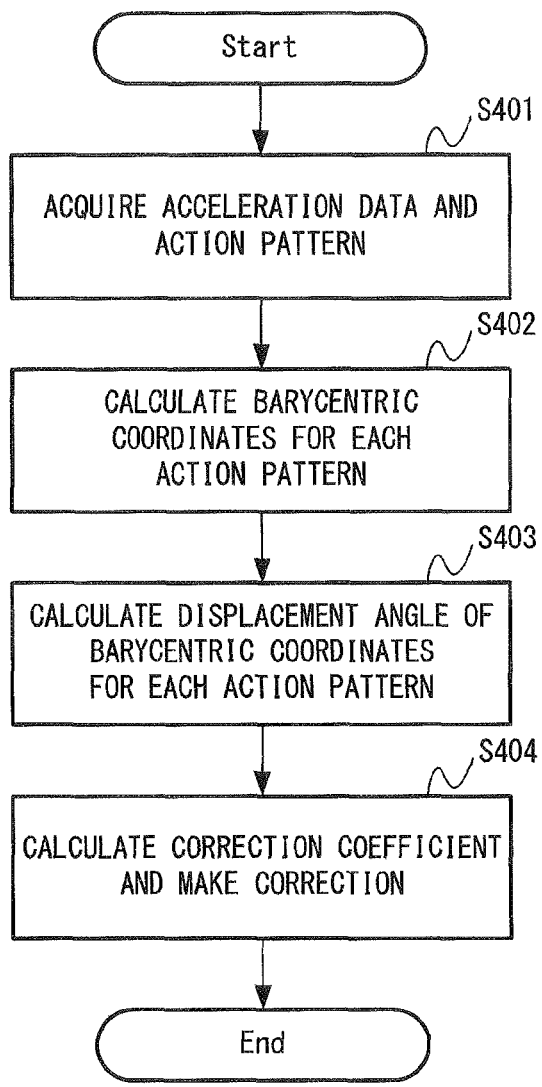
FIG. 8 is a flowchart showing the operation of a measurement system 100 according to a fourth embodiment.

The processing of the measurement device 110 according to the fourth embodiment is described hereinafter with reference to the flowchart of FIG. 8. Only the processing that is different from the first embodiment is mainly described below.

S401: Acquire Acceleration Data and Action Pattern

The input unit 111 of the measurement device 110 receives acceleration data that is transmitted from the sensor module 120 by wireless or wired communication. Note that it is preferred that the acceleration data is generated by the sensor module 120 and then transmitted to the measurement device 110 without delay.

At this time, a user observes the action of an object under test (a person or animal) and inputs information indicating the action pattern to the input unit 111 through the input device. For example, when the input device is a keyboard, keys corresponding to specified action patterns are defined in advance. To be more specific, a key R and a key W may be allocated to the actions of standing up and walking, respectively. Then, a user presses the key R when a person or animal as an object under test is standing up and presses the key W when the person or animal is walking.

The input unit 111 receives a user input indicting the action pattern of an object under test (a person or animal) from the input device. The input unit 111 then associates the acquired acceleration data with data indicating the action pattern input at that time (information about the pressed key in the case with the keyboard described above) and stores them into the storage device.

S402: Calculate Barycentric Coordinates for Each Action Pattern

The analysis unit 112 calculates, for each action pattern, the average value of all acceleration data associated with the action pattern by referring to the storage unit. Then, the x-direction component and the y-direction component of the average values of all data are defined as the actual barycentric coordinates of the action pattern.

S403: Calculate Displacement Angle of Barycentric Coordinates for Each Action Pattern

The analysis unit 112 calculates an angle θ between the predetermined ideal barycentric coordinates in the action pattern and the actual barycentric coordinates through the origin. For example, for the action pattern R, an angle $\theta_R$ between the ideal barycentric coordinates and the actual barycentric coordinates can be calculated by the equation (7). It is assumed that the ideal barycentric coordinates for each action pattern is prestored in the storage device.

$$\theta_R = \cos^{-1} \frac{X_R X_{RI} + Y_R Y_{RI}}{\sqrt{X_R^2 + Y_R^2}\sqrt{X_{RI}^2 + Y_{RI}^2}} \quad (7)$$

It is assumed that the ideal barycentric coordinates in the action pattern R are $(X_{RI}, Y_{RI})$, and the actual barycentric coordinates in the action pattern R are $(X_R, Y_R)$.

S404: Calculate Correction Coefficient and Make Correction

The analysis unit 112 calculates a correction coefficient in the action pattern R by using the displacement angle $\theta_R$ of the barycentric coordinates calculated in S403 and corrects the acceleration data for the action pattern R. In this embodiment, the analysis unit 112 corrects the acceleration data by the following equations (8) and (9).

$$a'_{X0} = a_{X0} \cos \theta_R + a_{Y0} \sin \theta_R \quad (8)$$

$$a'_{Y0} = -a_{X0} \sin \theta_R + a_{Y0} \cos \theta_R \quad (9)$$

In the above equations, $a'_{X0}$ and $a'_{Y0}$ are the x-component and the y-component of the corrected acceleration data for the action pattern R, $a_X$ and $a_Y$ are the x-component and y-component of the acceleration data (acquired in S401) before correction for the action pattern R, and $\cos \theta_R$ and $a_Y \sin \theta_R$ are correction coefficients for the action pattern R.

The analysis unit 112 performs the processing steps from S402 to S404 for every action pattern.

Note that, although the correction coefficient is calculated based on the displacement of the center of gravity in the two directions x and y in this embodiment, the correction coefficient may be calculated using the center of gravity in any two directions other than the above. Further, the correction coefficient may be calculated based on the displacement of the center of gravity in the three directions x, y and x. In the case of using the center of gravity in the three directions, the accuracy is improved but the amount of calculation increases compared with the case of using the center of gravity in the two directions.

Further, although the acceleration data is corrected in this embodiment, the average acceleration may be corrected, for example, depending on purpose.

Further, although the correction coefficient is calculated using the average value (barycentric coordinates) of acceleration data in this embodiment, the correction coefficient may be calculated using a given representative value other than the average value, for example, instead of using the average acceleration.

In this embodiment, the input unit 111 associates acceleration data with an action pattern, and the analysis unit 112 corrects the acceleration data using the displacement angle of the barycentric coordinates for each action pattern. It is thereby possible to make appropriate correction even when it is not appropriate that the distribution of acceleration data is approximated by a straight line. Particularly, because this example makes correction not on the statistical distribution of all data but by limiting the data to be processed to each action pattern, the accuracy increases.

Fifth Embodiment

A fifth embodiment has a feature that it performs correction by an alternative way in the case where linear approximation is not appropriate in the correction of acceleration data described in the first embodiment. Further, in comparison with the fourth embodiment, while correction according to the center of gravity for each action pattern is performed in the fourth embodiment, correction according to the center of gravity of all acceleration data is performed in the fifth embodiment.

The configuration of the measurement system 100 according to the fifth embodiment is substantially the same as that of the first embodiment and thus not redundantly described.

Figure 9:
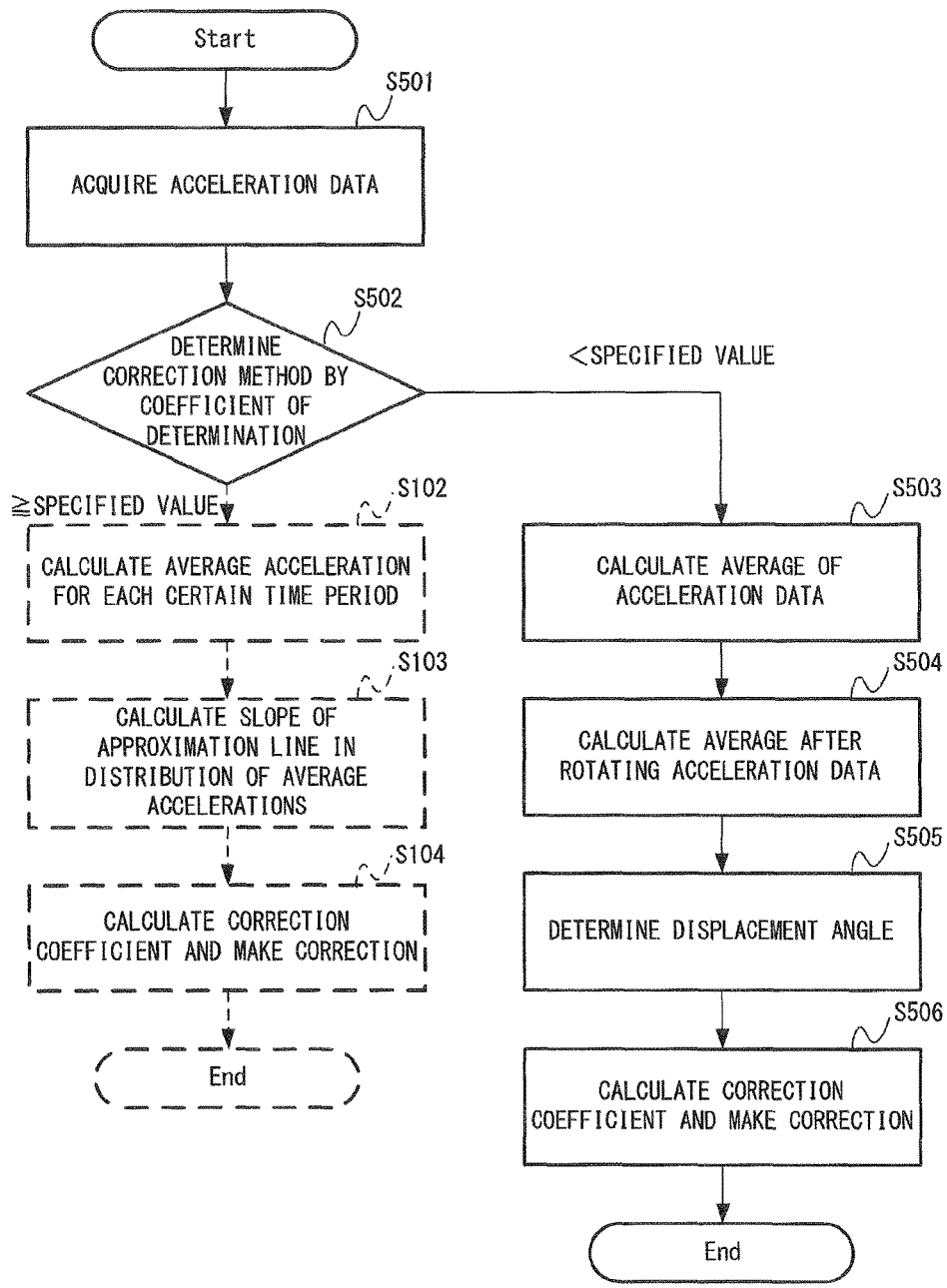
FIG. 9 is a flowchart showing the operation of a measurement system 100 according to a fifth embodiment.

The processing of the measurement device 110 according to the fifth embodiment is described hereinafter with reference to the flowchart of FIG. 9. Only the processing that is different from the first embodiment is mainly described below.

S501: Acquire Acceleration Data

The input unit 111 of the measurement device 110 receives acceleration data that is transmitted from the sensor module 120 by wireless or wired communication.

S502: Determine Correction Method by Coefficient of Determination

The input unit 111 calculates a coefficient of determination by the above-described equation (4). When the coefficient of determination is less than a specified value (for example, 0.3), the input unit 111 determines that it is not appropriate to perform linear approximation of average accelerations, and performs the correction by the method described later. On the other hand, when the coefficient of determination is equal to or more than the specified value, the input unit 111 determines that it is possible to perform linear approximation of average accelerations, and performs the correction by the method described in the first embodiment, for example.

S503: Calculate Average Value of Acceleration Data

The analysis unit 112 calculates the average value of components in an arbitrary direction (which is the y-direction in this example) for all acceleration data.

S504: Calculate Average Value after Rotating Acceleration Data

The analysis unit 112 rotates all acceleration data by the angle θ with respect to the origin on the x-y plane, and then calculates the average value of the y-direction component of the acceleration data again in the same manner as in S503. The y-direction component $a'_{Y0}$ when the acceleration data is rotated by the angle θ can be calculated by the following equation (10).

$$a'_{Y0} = -a_{X0} \sin \theta + a_{Y0} \cos \theta \quad (10)$$

The analysis unit 112 calculates the average value repeatedly by changing the angle θ with an increment of 10 degrees from −90 to +90 degrees, for example.

S505: Determine Displacement Angle

The analysis unit 112 compares the predetermined ideal average value $MM(a_{YI})$ (for example, 0) with a series of average values $M(a'_{Y0})$ calculated in S504 and specifies the angle θ at which the absolute value of the difference $|M(a'_{Y0}) - M(a_{YI})|$ is the smallest. It is assumed that the ideal average value is prestored in the storage device.

Figure 10:
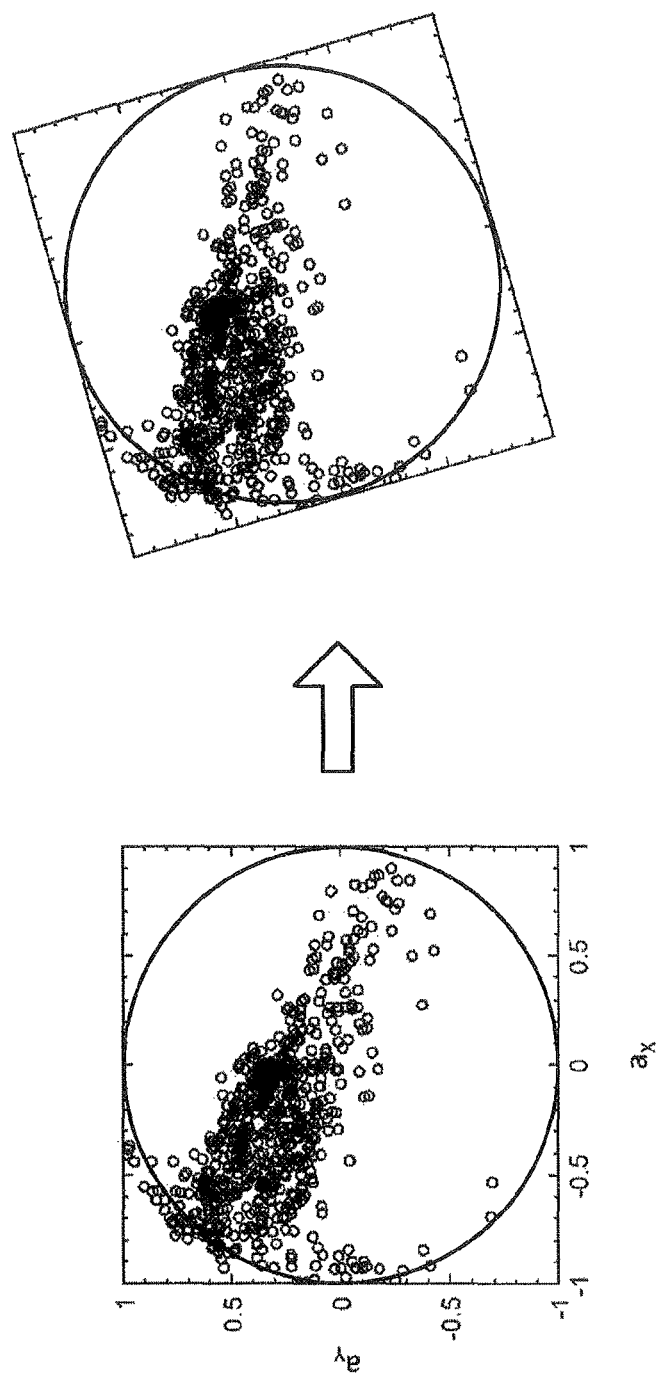
FIG. 10 is a view showing the concept of correction processing according to the fifth embodiment.
Figure 11:
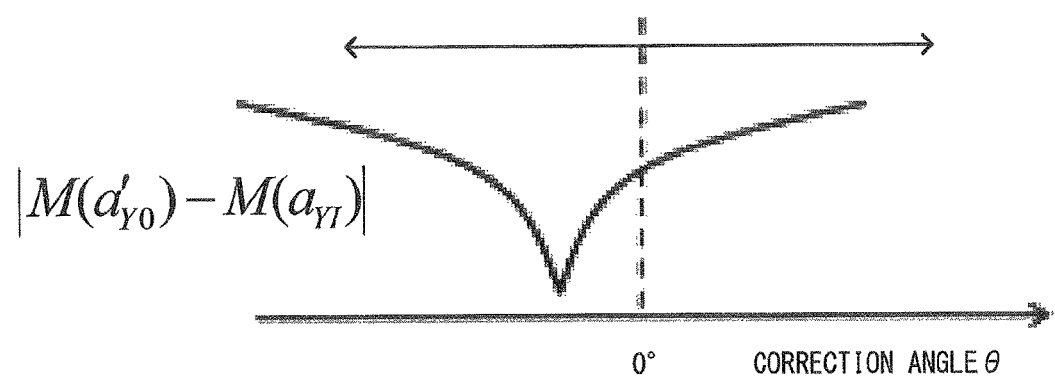
FIG. 11 is a view showing the concept of correction processing according to the fifth embodiment.

FIGS. 10 and 11 show the concept of this processing. The acceleration data plotted on the x-y plane is rotated by the angle θ with respect to the origin (FIG. 10). Then, the value of $|M(a'_{YO})-M(a_{YT})|$ changes with a change in the value of the angle θ, and it becomes the smallest at a certain value of θ (FIG. 11). In this embodiment, the value of θ at this time is regarded as the angle at which the displacement between the actual acceleration data and the ideal value is the smallest, and the correction using that value of θ is performed.

S506: Calculate Correction Coefficient and Make Correction

The analysis unit 112 calculates the correction coefficient using the displacement angle θ calculated in S505 and corrects the acceleration data. The correction of the acceleration data using the displacement angle can be made in the same manner as in the fourth embodiment, which is, by replacing $θ_R$ in the equations (8) and (9) with θ.

Note that, although the example that the input unit 111 performs the branching using the coefficient of determination (S502) is described in this embodiment, the correction after S503 may be performed directly without performing the branching.

Note that, although the correction coefficient is calculated based on the average value in the y-direction in this embodiment, the correction coefficient may be calculated using the average value in any one direction different from the above. Further, the correction coefficient may be calculated in the same manner based on the center of gravity in any two or three directions. In the case of using the center of gravity in two or three directions, the accuracy is improved but the amount of calculation increases compared with the case of using the average value in one direction.

Further, although the acceleration data is corrected in this embodiment, the average acceleration may be corrected, for example, depending on purpose.

Further, although the correction coefficient is calculated using the average value of acceleration data in an arbitrary direction in this embodiment, the correction coefficient may be calculated using a given representative value other than the average value, for example, instead of using the average acceleration.

In this embodiment, the analysis unit 112 performs correction according to the displacement of the average values of all acceleration data. It is thereby possible to appropriately correct the acceleration data even when linear approximation of the acceleration data is not appropriate.

Sixth Embodiment

Figure 12:
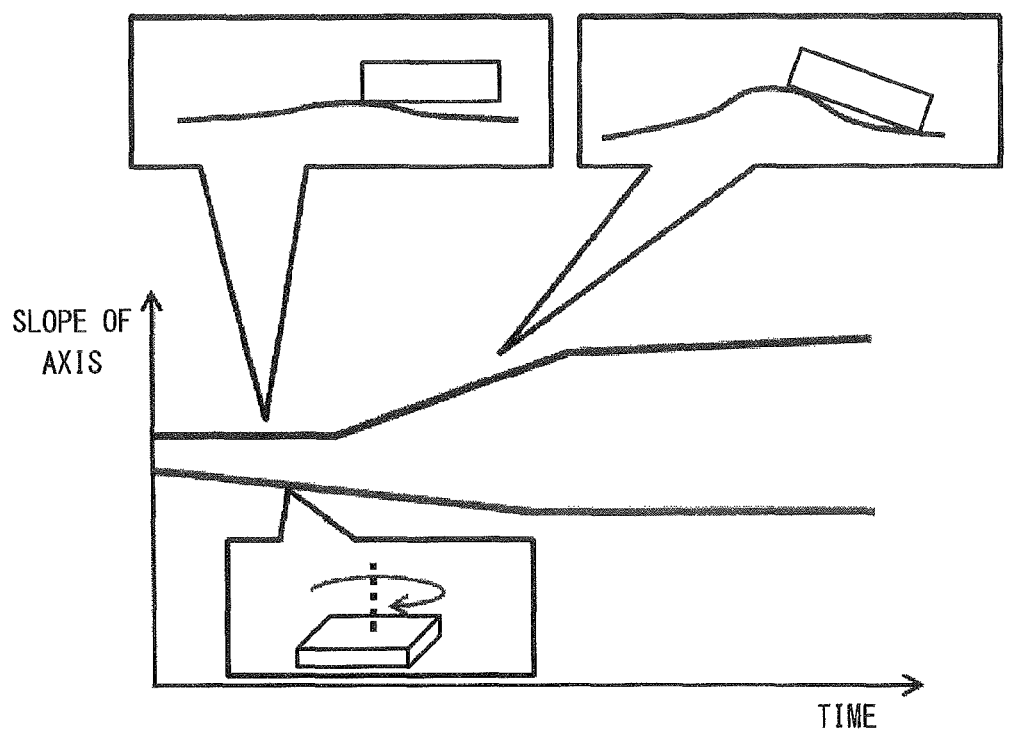
FIG. 12 is a view showing the concept of correction processing according to a sixth embodiment.

A sixth embodiment has a feature that the correction of acceleration data described in the first embodiment is performed at specified time intervals so that a change in the displacement of the axis can be observed. For example, in the case where the shape of an object under test changes with time or the case where the mounting direction or position of the acceleration sensor can change constantly with time, it is possible to generate time-series data indicating such a change (FIG. 12).

The configuration of the measurement system 100 according to the sixth embodiment is substantially the same as that of the first embodiment and thus not redundantly described.

Figure 13:
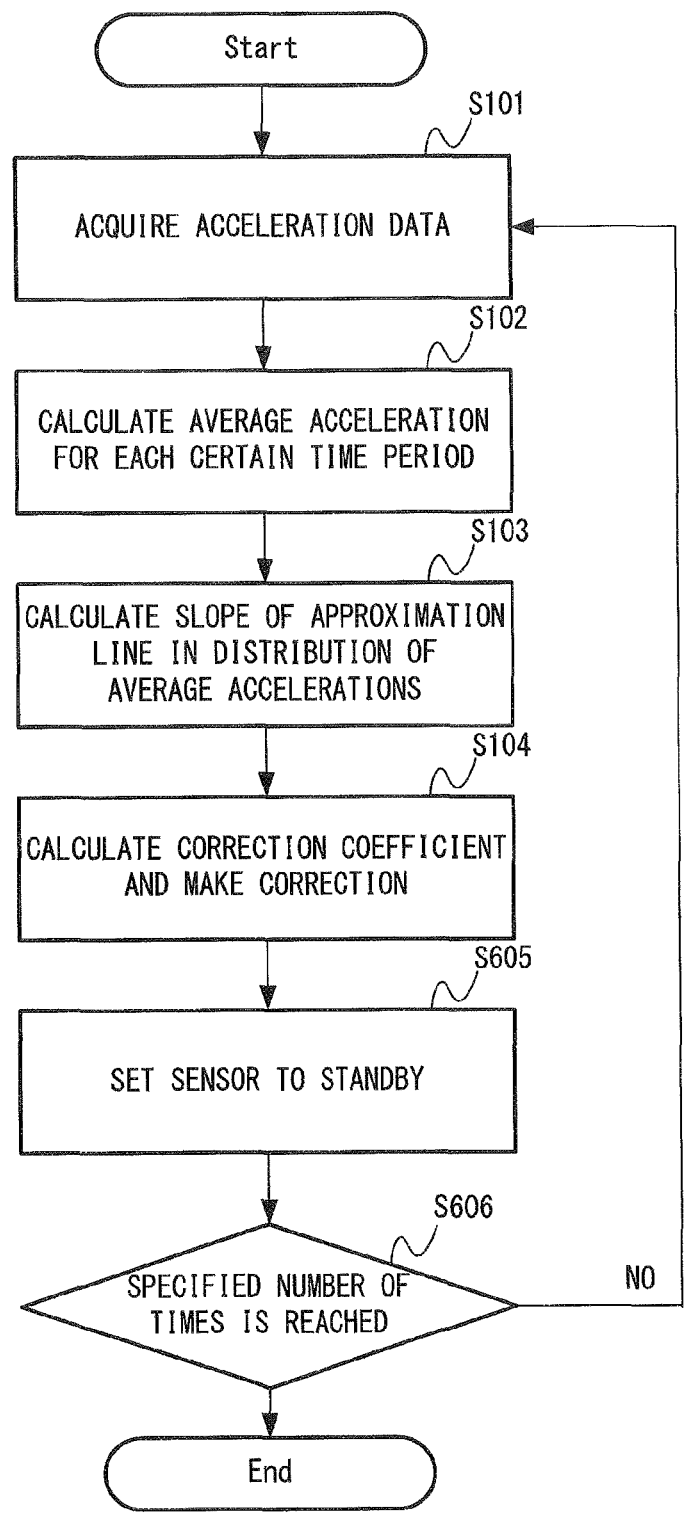
FIG. 13 is a flowchart showing the operation of a measurement system 100 according to the sixth embodiment.

The processing of the measurement device 110 according to the sixth embodiment is described hereinafter with reference to the flowchart of FIG. 13. Only the processing that is different from the first embodiment is mainly described below.

S101 to S104:

The input unit 111 of the measurement device 110 receives acceleration data that is transmitted from the sensor module 120 by wireless or wired communication. The analysis unit 112 calculates average acceleration for each certain time period and calculates the slope of a line that approximates the distribution of average accelerations. It then calculates a correction coefficient using the slope of the approximation line and corrects the average acceleration.

S605: Set Sensor to Standby

The analysis unit 112 stores the calculated slope of the approximation line, which is the displacement of the axis, into the storage device of the measurement device 110.

The input unit 111 transmits a standby instruction to the sensor module 120. The sensor module 120 receives the standby instruction and then stops the acquisition or transmission of acceleration data and transitions to standby mode.

S606: Start Up Sensor and Perform Repetition Processing

When a specified period of time has passed, the input unit 111 transmits a startup instruction to the sensor module 120. The sensor module 120 receives the startup instruction and then resumes the acquisition or transmission of acceleration data and performs a series of processing steps from S101 to S605 again. For example, when the specified period of time is 24 hours, the input unit 111 starts up the sensor module 120 every 24 hours and starts a process to calculate the axis displacement.

Further, the input unit 111 repeatedly performs the processing in S606 until reaching a specified number of times. For example, when the specified number of times is seven, the input unit 111 calculates the axis displacement each day for one week.

In this embodiment, the input unit 111 starts up the processing of calculating the axis displacement repeatedly every specified time, and it is thereby possible to generate a group of data indicating a change in the axis displacement over time. Thus, even when the fixation of the acceleration sensor to an object under test is not strong enough and the axis is likely to be displaced at all times, it is possible to correct the displacement of the axis each time. Further, when a part (for example, an affected part) of the body of a person or animal changes over time or a part (for example, a joint) of a structure such as a bridge or tunnel changes over time, the change can be observed by fixing the acceleration sensor to that part.

Seventh Embodiment

Figure 14:
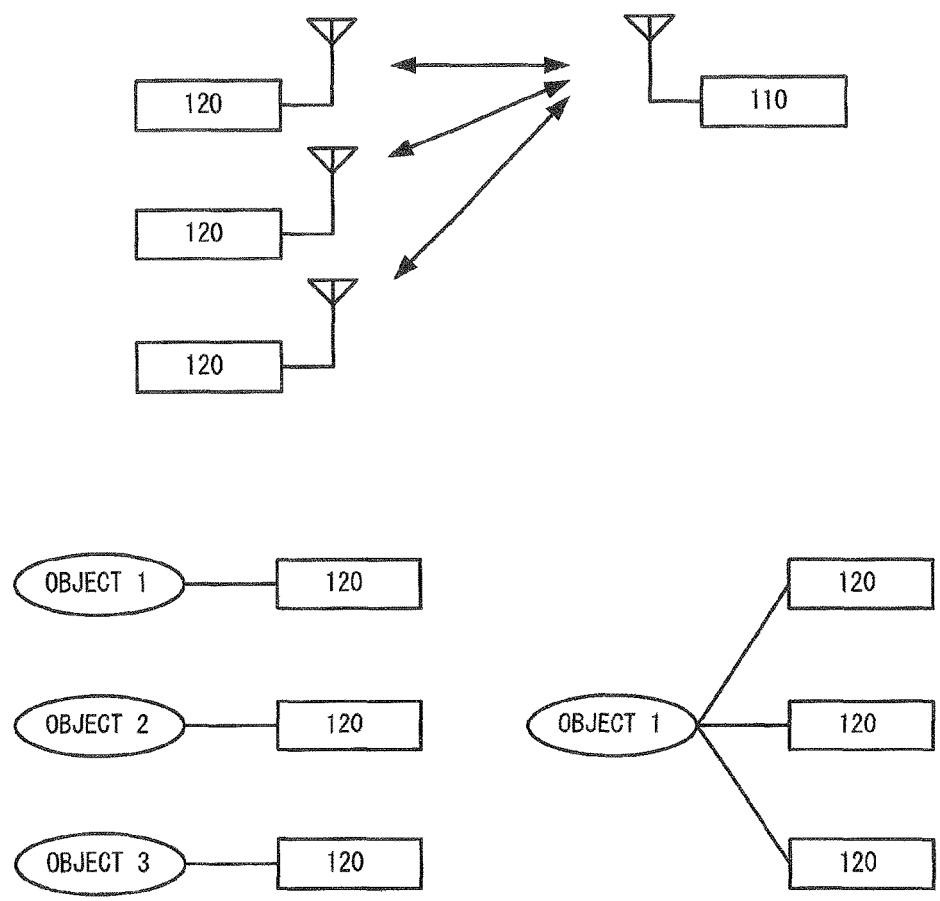
FIG. 14 is a view showing the configuration of a measurement system 100 according to a seventh embodiment.

The measurement system 100 according to a seventh embodiment has a feature that a plurality of sensor modules 120 are connected to one measurement device 110 (FIG. 14).

One sensor module 120 may be mounted on each of a plurality of objects under test, or a plurality of sensor modules 120 may be mounted on one object under test. For example, by mounting a plurality of sensor modules 120 in various parts of one person or animal, it is possible to detect the action of the person or animal in more detail.

The measurement device 110 communicates with a plurality of sensor modules 120 by time division, for example. Typically, the measurement device 110 corrects the acceleration data acquired from the respective sensor modules 120 independently of one another for each sensor module 120. Note that, when it is desirable to acquire a large amount of acceleration data by regarding a plurality of persons or animal as the same individual for the sake of classifying them by gender, age, weight and the like, for example, the correction may be performed by treating the acceleration data acquired from the plurality of sensor modules 120 as one set.

Other Embodiments

It should be noted that this embodiment is not limited to the above-described embodiments and may be varied in many ways within the scope of the present invention. For example, the configurations according to the second to sixth embodiments may be combined with another embodiment, not only the first embodiment.

Further, although the example that mounts the acceleration sensor mainly on a person or animal is described in the above embodiments, the acceleration sensor may be mounted on any object under test as a matter of course. For example, by mounting the acceleration sensor on a structure such as a bridge or tunnel and measuring a change in acceleration over time, it is possible to predict the aging.

Further, in the above embodiments, the example that uses the three-axis acceleration sensor as the sensor module 120 is mainly described. However, those embodiments may be applied to a single-axis acceleration sensor. For example, in the case of mounting a single-axis acceleration sensor to each of the head, back and leg of an animal as an object under test, the measurement device 110 can process the acquired three pieces of acceleration data in the same way as the three-axis acceleration data.

Eighth Embodiment

Figure 16:
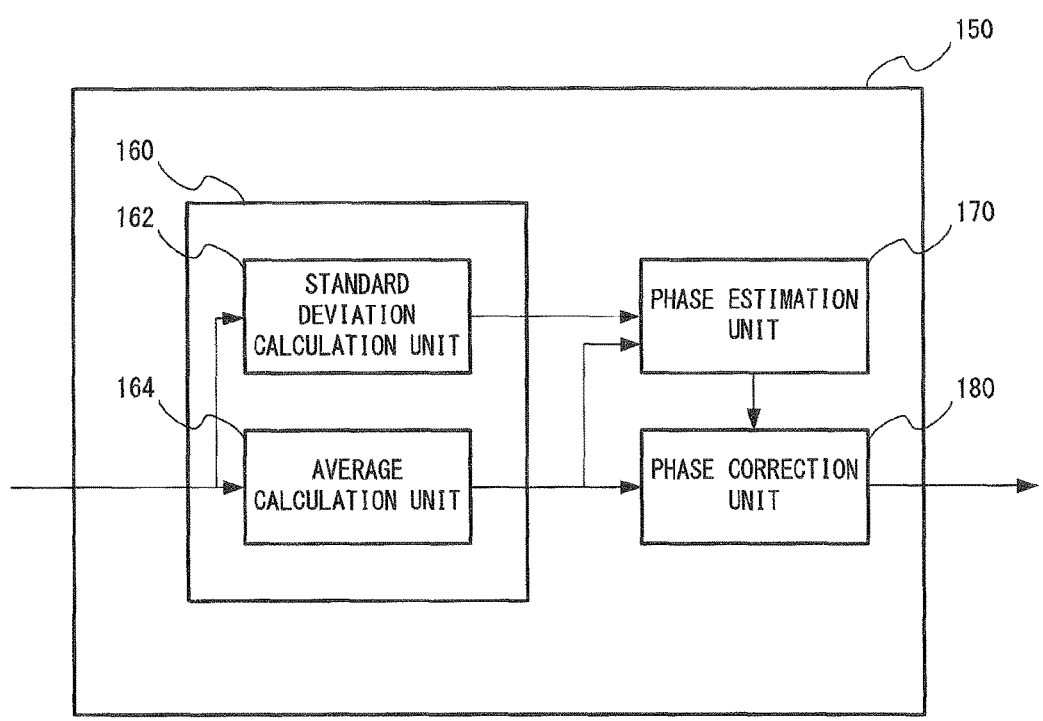
FIG. 16 is a view showing the configuration of a phase correction device 150 according to an eighth embodiment.

The configuration of a phase correction device 150 according to an eighth embodiment is described hereinafter with reference to FIG. 16.

The phase correction device 150 receives acceleration data that is output from the acceleration sensor (not shown) and performs phase correction of the acceleration data. The phase correction device 150 is typically an information processing device such as a PC (personal computer), a server computer or a microcontroller, and it is implemented by a CPU (Central Processing Unit), a storage device such as a volatile or nonvolatile memory, an input/output device and the like. The phase correction device 150 performs specified processing based on a program stored in the storage device and thereby logically implements a feature quantity estimation unit 160, a phase estimation unit 170 and a phase correction unit 180, which are described later.

Note that the acceleration sensor is mounted on an object, measures generated acceleration, and outputs acceleration data indicating a measured value. It is assumed that the acceleration data contain accelerations in three-axis (x-axis, y-axis and z-axis) directions.

The feature quantity estimation unit 160 receives the acceleration data and performs statistical processing. The feature quantity estimation unit 160 includes a standard deviation calculation unit 162 and an average calculation unit 164. The standard deviation calculation unit 162 calculates a standard deviation value of the acceleration data for each axis. The average calculation unit 164 calculates an average value of the acceleration data for each axis.

The phase estimation unit 170 performs bias correction and phase estimation of a specified axis by using the average values calculated by the average calculation unit 164 according to the standard deviation value that is calculated by the standard deviation calculation unit 162.

The phase correction unit 180 performs phase correction on the average values calculated by the average calculation unit 164 according to the phase estimation result by the phase estimation unit 170 and outputs a processing result.

The overview of a phase correction method of the phase correction device 150 according to the eighth embodiment is described hereinafter. This method performs the following procedure to make phase correction of the acceleration sensor.

First, the displacement of an angle from acceleration data that is obtained in an ideal placement state is estimated from the phase of actually acquired acceleration data, which is phase data that contains an error caused by the placement state of the acceleration sensor to an object. The ideal placement state is the state where the acceleration sensor is placed at a placement position where the characteristics of the action of an object are likely to emerge with the axes of the acceleration sensor coinciding with the directions that are likely to observe the characteristics of the action of the object, for example.

When estimating the phase of actually acquired acceleration data, it is desired to use the acceleration data when an object is in the state of rest. Thus, this embodiment extracts only the acceleration data during the period when the standard deviation of the acceleration data is less than a specified threshold and estimates the phase of the acceleration data.

Next, the phase of the actually obtained acceleration data is corrected. Specifically, the actually obtained acceleration data is corrected to a value that could have been obtained with the ideal placement state of the acceleration sensor.

This embodiment calculates the average value of acceleration data that is acquired during each certain time period, not the acquired acceleration data itself, and performs phase correction on the average value. By using a representative value of acceleration data in this manner, it is possible to suppress a load of the phase correction. Further, because the average value of acceleration data is a feature quantity that is suitable for action identification of an object, it is possible to use the average value after phase correction as it is for action identification.

The reason that the average value of acceleration data is suitable as a feature quantity for action identification is as follows. The present inventor has found that the distribution of the average values of acceleration data of each certain time period is deviated by the type of action (for example, movement, a change in posture etc.) of an object. Specifically, when the average values of the values of the x-axis and the y-axis of acceleration data are calculated every certain time period and those average values are plotted on the x-y axis, for example, there is a tendency that a group of each action type is formed in a different region on the coordinate plane.

Figure 17:
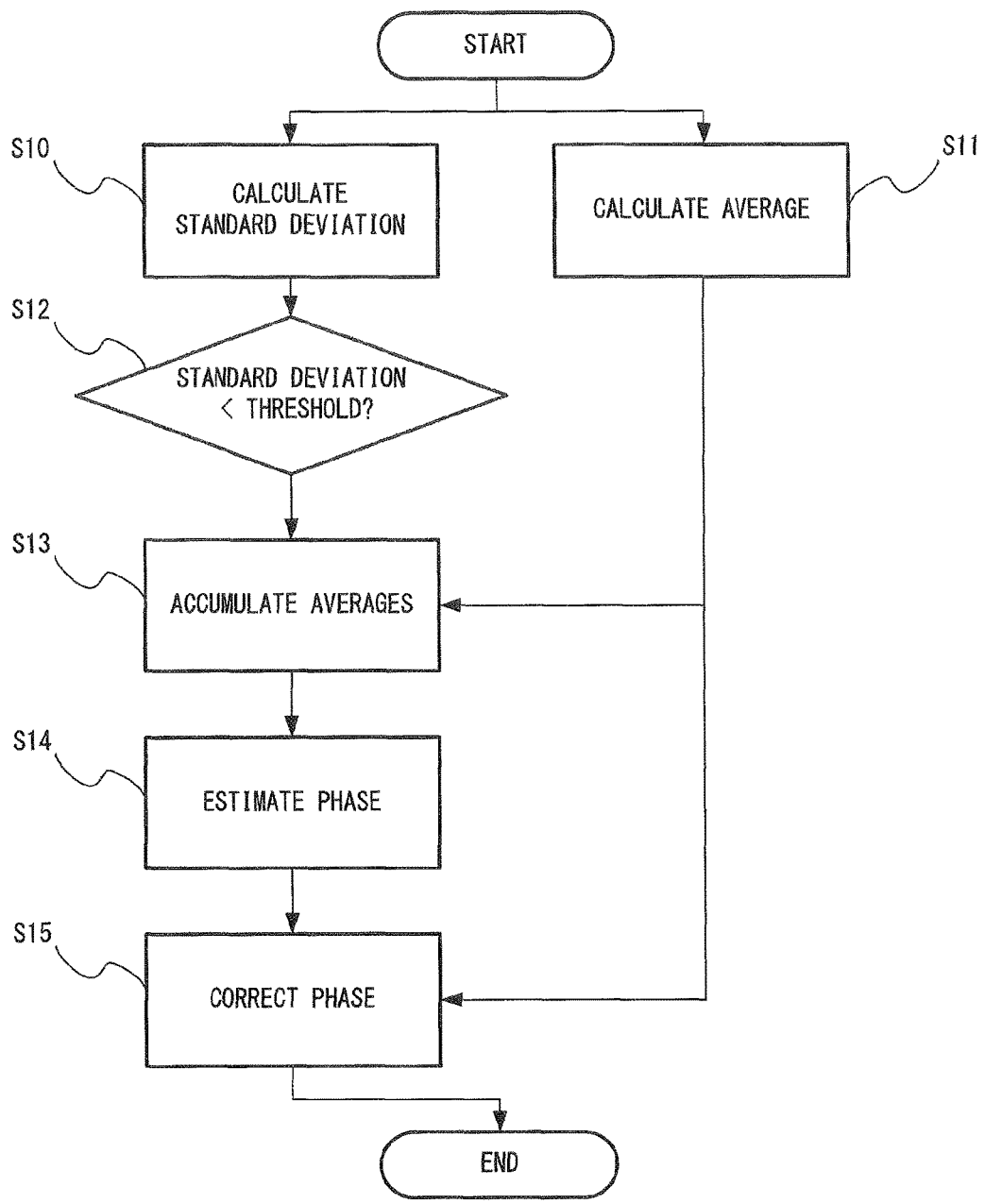
FIG. 17 is a view showing the operation of the phase correction device 150 according to the eighth embodiment.

The operation of the phase correction device 150 according to the eighth embodiment is described hereinafter with reference to the flowchart of FIG. 17.

S10:

Acceleration data is input from the acceleration sensor (not shown) to the standard deviation calculation unit 162 of the feature quantity estimation unit 160. Generally, the acceleration data is continuously input from the start to the end of measurement.

In this embodiment, the phase correction device 150 receives only the value aX in the x-direction and the value aY in the y-direction among the acceleration data. According to the knowledge of the present inventor, high accuracy can be achieved by using only aX and aY in any of the determination of the resting state and the action identification. Note that this embodiment is not limited thereto, and the same processing may be performed using values in other arbitrary two-axis or three-axis directions.

The standard deviation calculation unit 162 calculates, at every certain time interval (for example, one second), the standard deviation of a group of acceleration data input during that interval. The standard deviation calculation unit 162 repeats the calculation of the standard deviation.

S11:

Acceleration data is input from the acceleration sensor to the average calculation unit 164 of the feature quantity estimation unit 160, in parallel with the standard deviation calculation unit 162. Then, at every certain time interval (for example, one second), the average calculation unit 164 calculates the average value of acceleration data input during that interval. The average calculation unit 164 repeatedly performs the calculation of average value and outputs a result of the processing to the phase estimation unit 170 and the phase correction unit 180 each time.

S12:

The standard deviation calculation unit 162 determines whether the standard deviation calculated in S10 is smaller than a predetermined threshold. For example, when the standard deviation of a value in the x-axis direction is $\sigma_x$, the standard deviation of a value in the y-axis direction is $\sigma_y$, the threshold for a value in the x-axis direction is TH1, and the threshold for a value in the y-axis direction is TH2, the above-described determination can be made by the following equation (11). When it is determined as "YES" in the equation (11), the phase estimation unit 170 performs the processing of S13.

$$\text{if } (\sigma_X < TH1 \& \sigma_y < TH2) \text{ then YES} \tag{11}$$

S13:

The average value calculated by the average calculation unit 164 is input to the phase estimation unit 170 at certain time intervals. Further, a notification indicating that the standard deviation is smaller than a threshold is input as needed from the standard deviation calculation unit 162. When this notification is input, the phase estimation unit 170 stores the average value that is input at the same timing into a register. The phase estimation unit 170 repeats this storage process until a specified number of average values are accumulated in the register.

Although the number of times of accumulating average values may be set arbitrarily, the accuracy of phase estimation increases as the number of times of accumulation increases.

S14:

The phase estimation unit 170 performs bias correction and phase estimation on the specified number of average values accumulated in the register.

Figure 18:
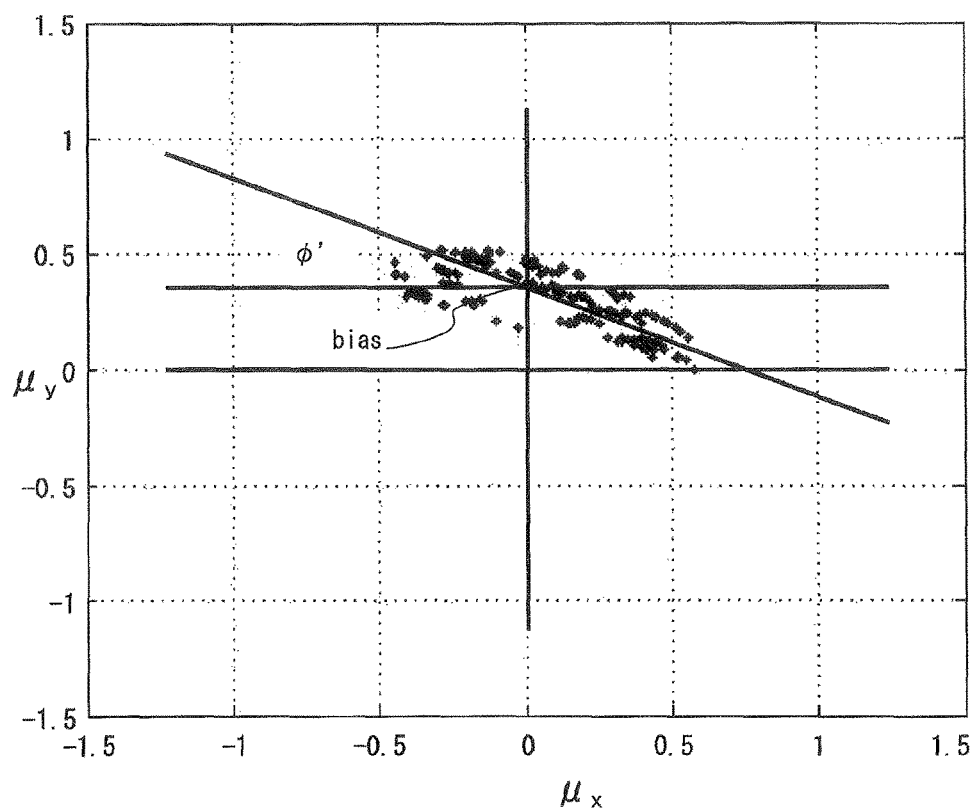
FIG. 18 is a view showing the overview of phase correction processing according to the eighth embodiment.

To illustrate this processing, FIG. 18 shows the example in which the average values stored in S13 are plotted in the x-y coordinates. The distance between the intersection between the approximation line of those average values and the y-axis and the origin is referred to as bias. The bias correction is the operation that makes the intersection and the origin coincide with each other. Further, the angle φ' between the approximation line and the line y=bias is referred to as phase. The phase correction is the operation that corrects the phase φ' to 0.

In this embodiment, the bias is calculated in a simplified manner by the following way. The phase estimation unit 170 extracts average values in proximity to the y-axis, and calculates the average of the y-coordinates of those average values as the bias. This calculation is represented by the following equation (12). In this equation, TH3 is a threshold that defines the proximity range to the y-axis, $\rho_x(i)$ is the x-coordinate of each average value, and $\mu_y(i)$ is the y-coordinate of each average value. Further, $\mu_{y2}(i)$ is the y-coordinate of each average value after bias correction.

$$\text{if } (\text{abs}(\mu_x(i)) < TH3) \tag{12}$$

$$\mu_{ysum} = \sum \mu_y(i)$$

$$\text{bias} = \frac{\mu_{ysum}}{N}, \mu_{y2}(i) = \mu_y(i) - \text{bias}$$

Further, in this embodiment, the phase is calculated in a simplified manner by the following way. First, the phase estimation unit 170 calculates the average coordinates of the average values which have been bias-corrected and whose x-coordinates are on the negative side. This calculation is represented by the following equation (13). Then, the phase estimation unit 170 calculates the angle $\varphi_1$ between the average coordinates and the origin. This calculation is represented by the following equation (14).

$$\text{if}(\mu_x(i) < 0) \tag{13}$$

$$\mu_{xave1} = \frac{\sum \mu_x(i)}{M1}, \mu_{y2ave1} = \frac{\sum \mu_{y2}(i)}{M1}$$

$$\phi_1 = a\tan2(\mu_{y2ave1}, \mu_{xave1}) \tag{14}$$

Likewise, the phase estimation unit 170 calculates the average coordinates of the average values which have been bias-corrected and whose x-coordinates are on the positive side. This calculation is represented by the following equation (15). Then, the phase estimation unit 170 calculates the angle $\varphi_2$ between the average coordinates and the origin. This calculation is represented by the following equation (16).

$$\text{if}(\mu_x(i) > 0) \tag{15}$$

$$\mu_{xave2} = \frac{\sum \mu_x(i)}{M2}, \mu_{y2ave2} = \frac{\sum \mu_{y2}(i)}{M2}$$

$$\phi_2 = a\tan2(\mu_{y2ave2}, \mu_{xave2}) \tag{16}$$

Finally, the phase estimation unit 170 averages the angles $\varphi_1$ and $\varphi_2$ and thereby obtains the phase φ'. This calculation is represented by the following equation (17).

$$\phi' = \frac{(\pi - \phi_1) + (0 - \phi_2)}{2} \tag{17}$$

Figure 19:
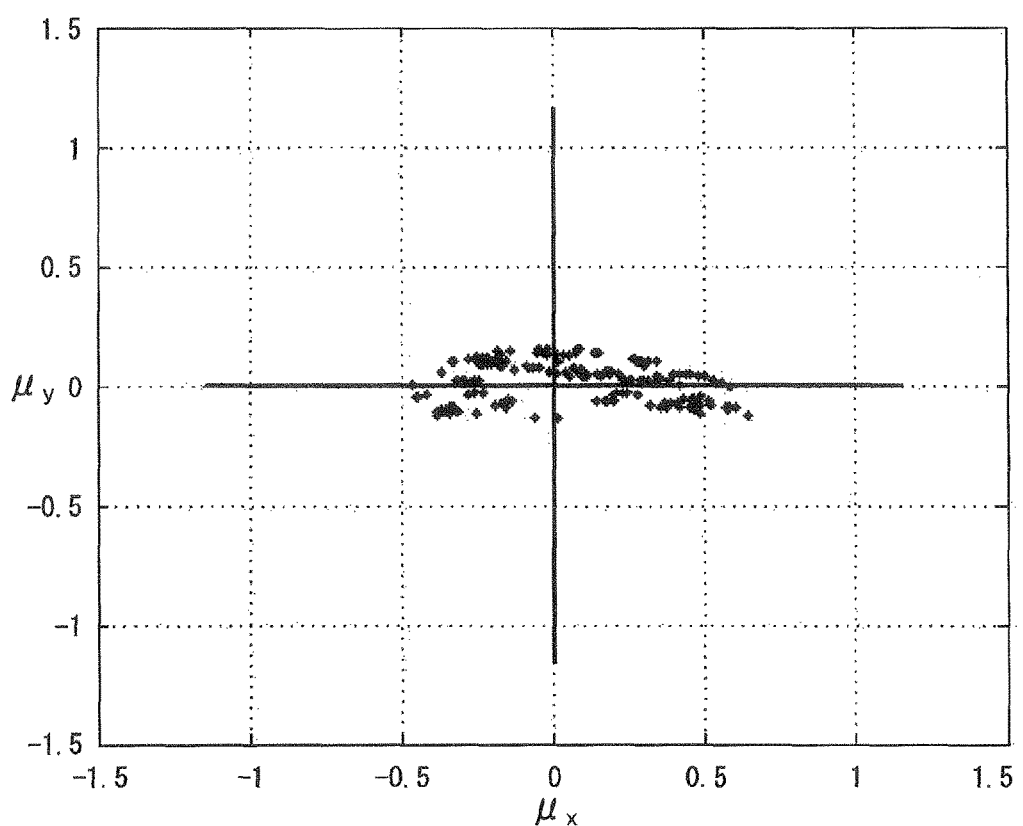
FIG. 19 is a view showing the overview of phase correction processing according to the eighth embodiment.

S15:

The phase correction unit 180 performs phase correction of each average value after the bias correction by using the phase φ' that is calculated in S14. This calculation is represented by the following equation (18). Further, FIG. 19 shows the example in which the average values after the phase correction in S15 are plotted in the x-y coordinates.

$$\mu'_x(i) = \mu_x(i) \cdot \cos(\phi') - \mu_{y2}(i) \cdot \sin(\phi')$$

$$\mu'_y(i) = \mu_x(i) \cdot \sin(\phi') - \mu_{y2}(i) \cdot \cos(\phi') \tag{18}$$

Preferably, the phase correction device 150 repeatedly performs a series of processing steps from S10 to S15 periodically, for example, for a measurement period of acceleration data.

According to this embodiment, the phase estimation unit 170 estimates the displacement of the mounting position and direction of the acceleration sensor as a phase. Further, the phase correction unit 180 corrects the estimated phase. It is thereby possible to correct the displacement of the mounting position and direction of the acceleration sensor that can occur due to individual differences or the lapse of time and obtains the acceleration data that is always in substantially the same phase only by the statistical processing of acceleration data without performing calibration of the acceleration sensor. Thus, if a threshold or a machine learning parameter for action identification is calculated once, the same threshold or machine learning parameter can be used in common even for the acceleration data obtained from another individual or the acceleration data where the phase displacement occurs due to long-term measurements.

Further, in this embodiment, the phase estimation unit 170 performs estimation of a bias and estimation of a phase in simplified ways as described above. Further, the phase correction process is performed using the average value of acceleration data for each certain time period. It is thereby possible to suppress the processing load and achieve the high-speed phase correction.

Ninth Embodiment

Figure 22:
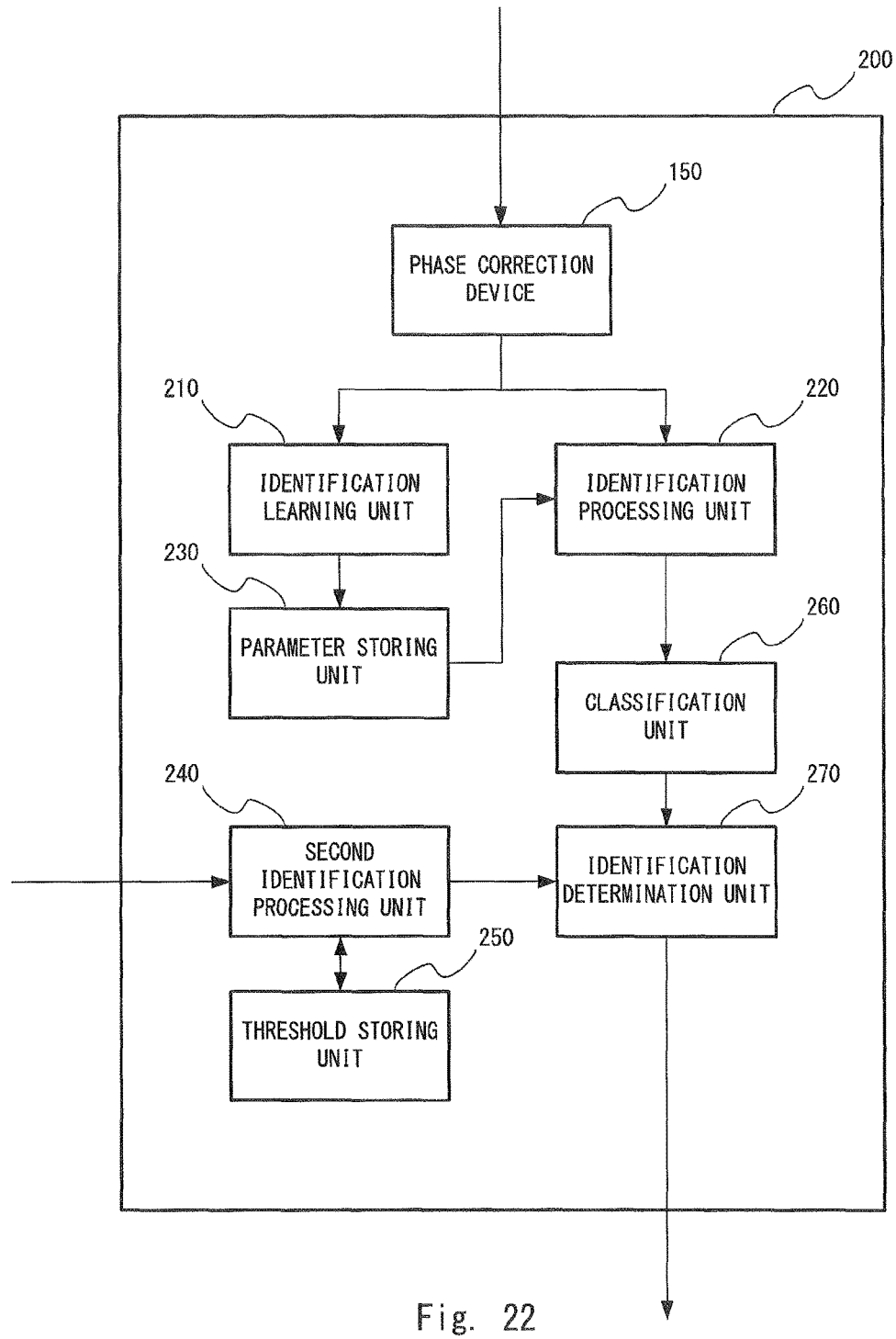
FIG. 22 is a view showing the configuration of an action identification device 200 according to the ninth embodiment.

A ninth embodiment relates to an action identification device 200 that includes a phase correction device 150. First, the configuration of the phase correction device 150 according to the ninth embodiment is described hereinafter with reference to FIG. 22.

The action identification device 200 receives acceleration data that is output from the acceleration sensor and performs processing to identify the action of an object by using the phase-corrected acceleration data. The action identification device 200 is typically an information processing device such as a PC (personal computer), a server computer or a microcontroller, and it logically implements a phase correction device 150, an identification learning unit 210, an identification processing unit 220, a parameter storing unit 230, a second identification processing unit 240, a threshold storing unit 250, a classification unit 260, and an identification determination unit 270 by executing specified processing based on a program stored in the storage device.

Note that, although the action identification device 200 is implemented to be integral with the phase correction device 150 by way of illustration in this embodiment, the action identification device 200 and the phase correction device 150 may be separate devices. In this case, the action identification device 200 receives the acceleration data that has been phase-corrected by the phase correction device 150 and performs action identification.

The phase correction device 150 receives the acceleration data that is generated by the acceleration sensor and performs the phase correction by the procedure described in the eighth embodiment.

The identification learning unit 210 performs learning using the phase-corrected acceleration data and thereby produces the identification processing unit 220 as a discriminator that identifies action types. Typically, the identification learning unit 210 and the identification processing unit 220 are implemented by SVM (Support Vector Machine). Note that the identification learning unit 210 and the identification processing unit 220 can be substituted by other known learning and identification mechanism as a matter of course.

The parameter storing unit 230 is a storage region that stores a parameter for the identification processing unit 220 (which is the SVM in this embodiment) to operate. Note that a specific parameter that can be used for the operation of a discriminator such as the SVM is already known and thus not redundantly described.

The classification unit 260 classifies the average values of the acceleration data into action types (classes) identified by the identification processing unit 220 and stores them.

The second identification processing unit 240 performs processing to identify the action types of acceleration data by a different way from the identification learning unit 210 and the identification processing unit 220. In this embodiment, the second identification processing unit 240 extracts the acceleration data that is related to a specific action type by using time-axis cross-correlation properties.

The threshold storing unit 250 stores a threshold that is used for action identification that is performed by the second identification processing unit 240. Specifically, the second identification processing unit 240 performs action identification by using the threshold stored in the threshold storing unit 250.

The identification determination unit 270 puts together action identification results that are stored in the classification unit 260 and action identification results that are output from the second identification processing unit 240 and thereby performs highly accurate action identification and outputs an identification result.

Figure 23:
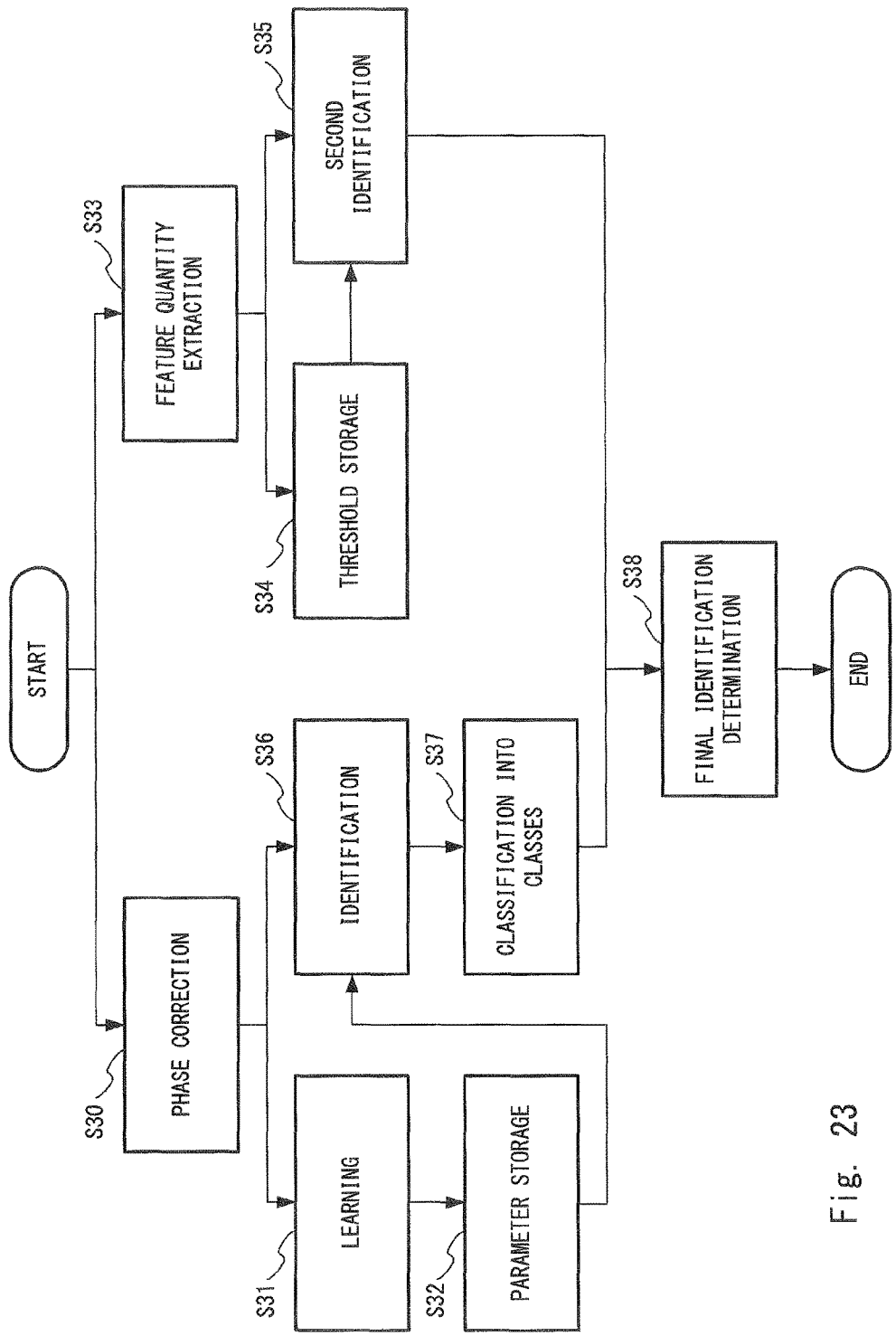
FIG. 23 is a view showing the operation of the action identification device 200 according to the ninth embodiment.

The operation of the action identification device 200 is described hereinafter with reference to the flowchart of FIG. 23.

S30:

The phase correction device 150 receives acceleration data from the acceleration sensor and performs phase estimation and phase correction on the average values of the acceleration data. In this embodiment, it performs phase correction on the average values for each certain time period of all acceleration data input from the acceleration sensor.

Figure 20:
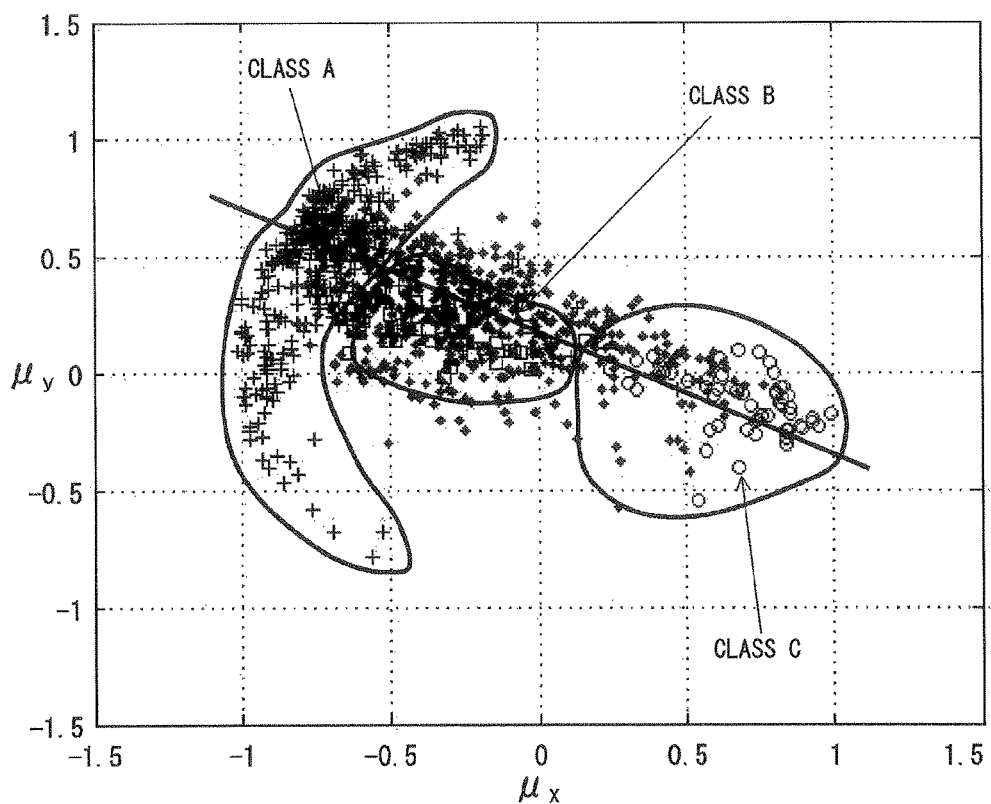
FIG. 20 is a view showing the overview of phase correction processing according to a ninth embodiment.

In FIG. 20, the average values of all acceleration data before phase correction by the phase correction device 150 are plotted in the x-y coordinates. As described also in the eighth embodiment, a bias and a phase occur also in FIG. 20. Those bias and phase differ by each individual of an object and further indicate different values depending on the position where the acceleration sensor is placed. Therefore, even when an action identification parameter is calculated from the acceleration data acquired in a certain individual, this parameter cannot be applied to the action identification by the acceleration data acquired in another individual. For example, the sample of FIG. 20 includes the acceleration data belonging to three action types: classes A, B and C. When discriminating among those three classes, it is needed to calculate parameters for discriminating between the classes A and B and between classes B and C, respectively. Further, the specification of those parameters needs to be performed for each individual and each measurement.

Figure 21:
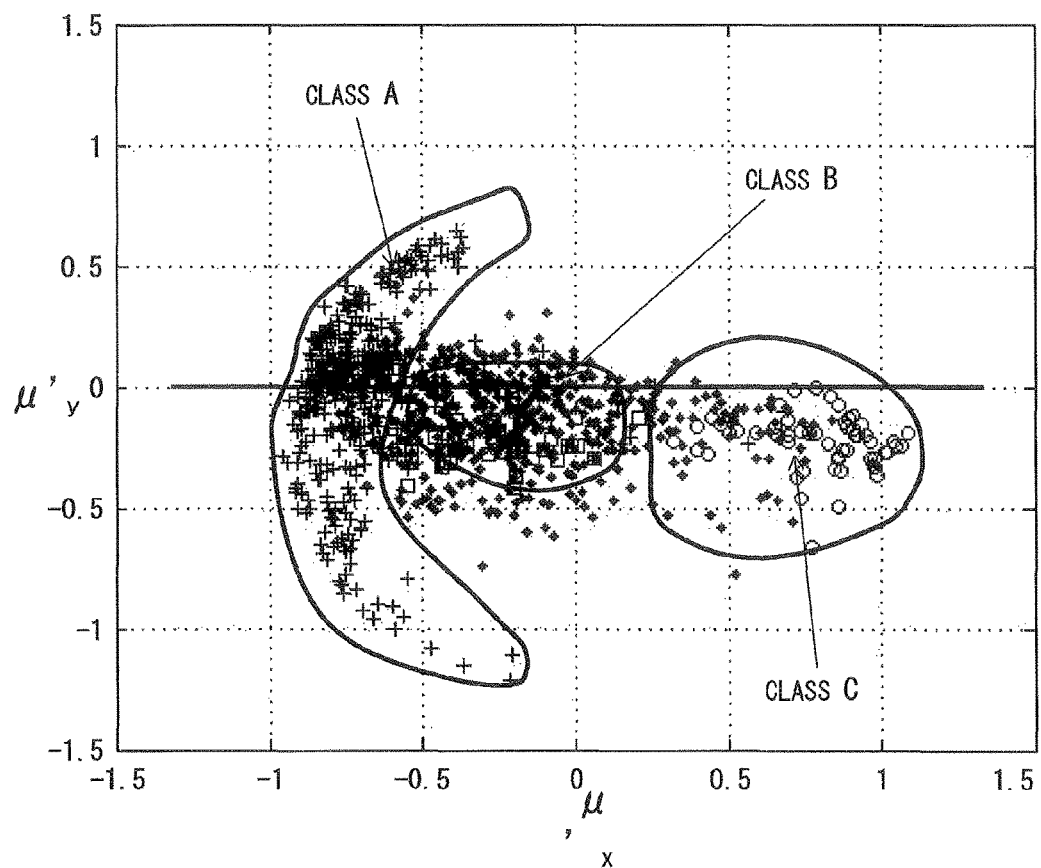
FIG. 21 is a view showing the overview of phase correction processing according to the ninth embodiment.

On the other hand, in FIG. 21, the average values of all acceleration data after phase correction by the phase correction device 150 are plotted in the x-y coordinates. If an action identification parameter is calculated once using those phase-corrected acceleration data, it is possible to apply this parameter to the action identification even when a phase displacement occurs in each individual or each identification.

The phase correction device 150 outputs the average values of acceleration data after phase correction to the identification learning unit 210 or the identification processing unit 220. When the subsequent processing is creation of a discriminator, which is, learning (S31), the phase correction device 150 outputs them to the identification learning unit 210. On the other hand, when the discriminator is already created and the subsequent processing is action identification (S36), the phase correction device 150 outputs them to the identification processing unit 220.

<Learning Processing>

S31:

The identification learning unit 210 inputs the average values of acceleration data after phase correction to the SVM. The SVM thereby generates a parameter indicating the most appropriate boundary for classifying the input average values into action types.

The SVM is a discriminator that discriminates between two classes. Thus, in the case of discriminating among three or more classes of action types, it is necessary to combine a plurality of discriminators that discriminate between two classes. For example, in order to discriminate among the three classes A, B and C, a discriminator 1 that discriminates between the classes A and B and a discriminator 2 that discriminates between the classes B and C are created. Thus, the creation of a discriminator is performed two times.

S32:

The identification learning unit 210 stores the parameter for the discriminator created in S31 into the parameter storing unit 230. Note that, in the case where a plurality of discriminators are created in S31, parameters for the respective discriminators are stored.

<Action Identification>

S33:

The second identification processing unit 240 receives acceleration data from the acceleration sensor and extracts a specified feature quantity that can be used for improving identification accuracy. Further, it performs action identification by using the feature quantity.

For example, when there is a feature quantity capable of specifying only the fact that acceleration data belongs to the class B, the second identification processing unit 240 can extract it. In this case, if the logical AND is carried out between identification results of the identification processing unit 220 and identification results of the second identification processing unit 240 in the subsequent processing, the action identification with higher accuracy can be achieved for the class B compared with the case of using either one identification processing unit only.

Accordingly, the feature quantity that is extracted in this step is preferably different from the one used by the identification processing unit 220. For example, the present inventor has found that, when an object is walking, the time-axis cross-correlation properties of the acceleration data become characteristic. To be specific, periodic data having the characteristics of the walking operation (for example, SIN waveform with several Hz) is first generated arbitrarily. Next, the second identification processing unit 240 calculates a cross-correlation value between the periodic data and the acceleration data. When the cross-correlation value is larger than a specified threshold, the second identification processing unit 240 determines that those acceleration data indicate the walking operation. Note that, in order to increase the detection accuracy, an action may be detected in the case where the number of times the cross-correlation value exceeds the threshold is equal to or more than a specified number.

S34:

The second identification processing unit 240 stores a threshold required for identifying an action type by the feature quantity extracted in S33 into the threshold storing unit 250.

S35:

The second identification processing unit 240 performs action identification by using the feature quantity extracted in S33 and the threshold stored in the threshold storing unit 250.

S36:

The identification processing unit 220 inputs the average value of acceleration data after phase correction into the SVM. The SVM thereby identifies an action type or class to which the input average value belongs and outputs the result to the classification unit 260.

Note that, in the case of discriminating among three or more classes of action types, it is necessary to combine a plurality of discriminators that discriminate between two classes. For example, in order to discriminate among the three classes A, B and C, action identification is performed two times using a discriminator 1 that discriminates between the classes A and B and a discriminator 2 that discriminates between the classes B and C.

S37:

The classification unit 260 holds classification results in S36.

S38:

The identification determination unit 270 puts together action identification results held by the classification unit 260 and action identification results by the second identification processing unit 240 and thereby perform final action identification.

For example, it is assumed that the classification unit 260 holds which of the three classes A, B and C is identified in S36, and the second identification processing unit 240 holds whether the class B is identified or not in S35. In this case, the identification determination unit 270 carries out the logical AND between identification results held in the classification unit 260 and identification results held in the second identification processing unit 240. Then, only when both of the classification unit 260 and the second identification processing unit 240 have the determination result indicating the class B, the identification determination unit 270 determines the final identification result as the class B. Therefore, for the class B, highly accurate action identification can be achieved compared with the case of using either one identifier only. In other words, the identification determination unit 270 can filter the identification result of the SVM using the identification result of the second identification processing unit 240.

Note that, for the class for which action identification is not performed by the second identification processing unit 240, the identification result that is stored in the classification unit 260 may be output as it is.

In this embodiment, the phase correction device 150 performs phase correction of the average values of acceleration data, and the identification learning unit 210 and the identification processing unit 220 perform action identification by using the average values after the phase correction. Thus, a class identification parameter that is calculated once can be applied to another individual and measurement, and it is thereby possible to improve the efficiency of action identification.

Further, in this embodiment, the identification determination unit 270 puts together the identification results identified by the identification processing unit 220 and the identification results by the second identification processing unit 240 and thereby outputs the final identification result. It is thereby possible to achieve highly accurate action identification.

Tenth Embodiment

A tenth embodiment has a feature that the efficiency of learning and identification are improved in the identification learning unit 210 and the identification processing unit 220 according to the ninth embodiment.

Figure 24:
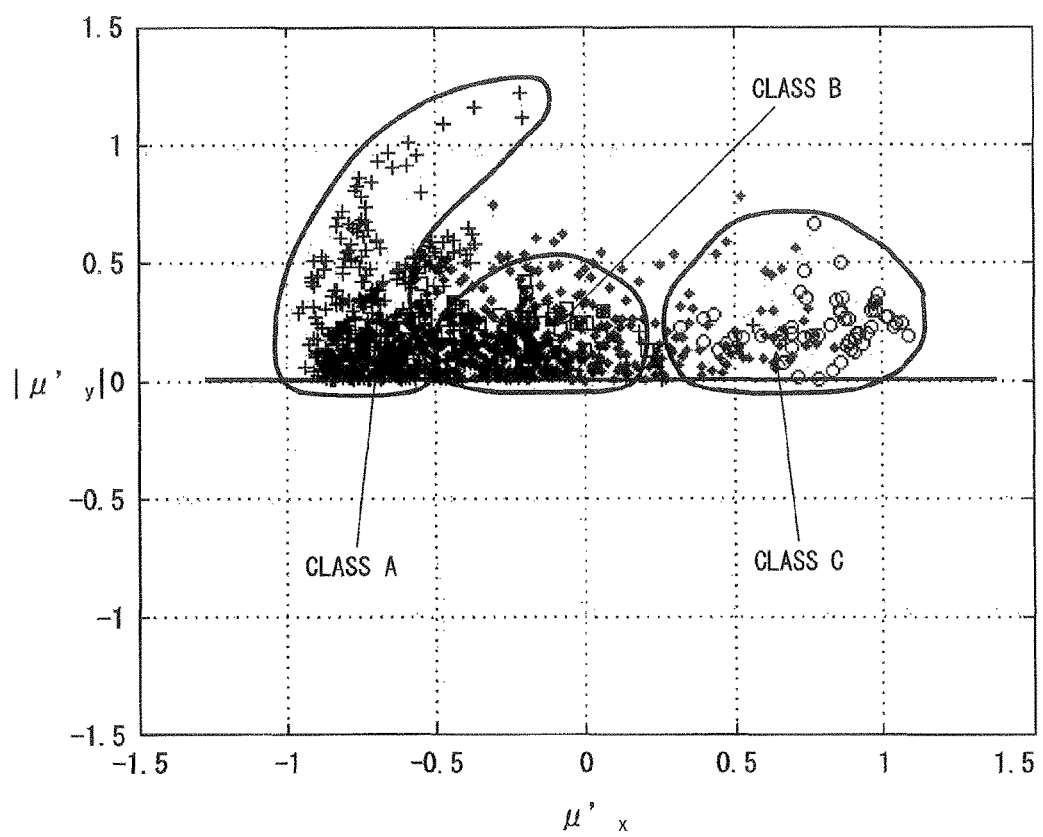
FIG. 24 is a view showing the overview of action identification processing according to a tenth embodiment.

The overview of the processing according to the tenth embodiment is described with reference to FIGS. 21 and 24. First, consider the case where the average values of acceleration data in the distribution shown in FIG. 21 are input to the identification learning unit 210 and the identification processing unit 220 to perform learning and identification. In this example, the distribution range of the class A is large, and therefore the number of SV (support vectors) that defines the range of the class is likely to be large. In this case, the learning accuracy can be degraded depending on the number of samples to be learned.

Thus, in this embodiment, processing of producing an absolute value is added for a value on the vertical axis side (a value in the y-axis direction) among the average values of acceleration data. The distribution of the average values of acceleration data after such processing is shown in FIG. 24. In FIG. 24, the sample distribution range is reduced to about half compared with FIG. 21. Accordingly, the number of SV for defining the range of a class decreases. In addition, the number of samples existing in the class distribution range, which is the density of samples, increases to about double.

The action identification device 200 according to the tenth embodiment has the feature in which the phase correction device 150 outputs average values of acceleration data after phase correction. The other configuration is the same as in the ninth embodiment and thus not redundantly described.

The operation of the action identification device 200 in the tenth embodiment is described hereinafter with reference back to the flowchart of FIG. 23. Note that only a different operation from the ninth embodiment is mainly described below, and the other operation is not redundantly described.
S30:

The phase correction device 150 receives acceleration data from the acceleration sensor and performs phase estimation and phase correction on the average value of the acceleration data. Further, for the average value of the acceleration data after phase correction, the phase correction unit 180 of the phase correction device 150 updates a value in a specified axis direction to the absolute value of that value.

The specified axis can be determined based on the expected distribution status of average values of acceleration data. For example, when the average values of acceleration data are distributed to be substantially symmetrical to the x-axis as shown in FIG. 21, the advantageous effects of this embodiment can be exerted most effectively by producing the absolute value for the value in the y-axis direction.

The phase correction device 150 outputs the average values of acceleration data after the update to the identification learning unit 210 or the identification processing unit 220. After that, the processing steps of S31 to S38 are performed in the same manner as in the second example. Note that it is not necessary to use the above-described average values in the identification in the processing steps S33 to S35.

In this embodiment, the phase correction unit 180 produces the absolute value of a value in a specified axis direction for the average values of acceleration data. The number of samples in the distribution range of a class thereby increases to improve the learning accuracy. Further, because the length of an identification support vector becomes shorter, it is possible to reduce the amount of calculation for identification.

Eleventh Embodiment

Figure 25:
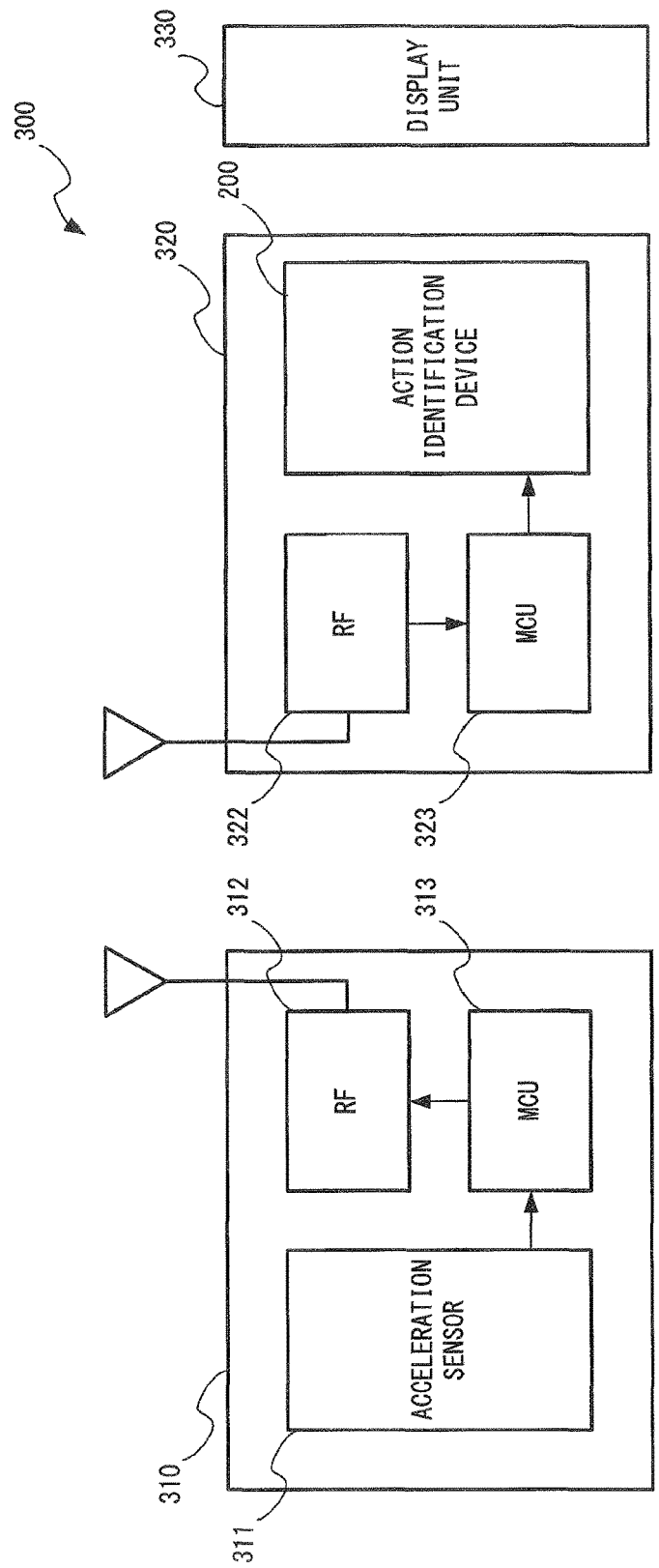
FIG. 25 is a view showing the configuration of an action identification system 300 according to an eleventh embodiment.

An eleventh embodiment describes one example of an action identification system 300 that includes the action identification device 200. FIG. 25 shows a configuration example of the action identification system 300.

A transmitting unit 310 is used by being mounted on an object under test, and measures generated acceleration and outputs acceleration data indicating a measured value. The transmitting unit 310 includes an acceleration sensor 311, an MCU (Micro Control Unit) 313 that generates acceleration data from an output signal of the acceleration sensor and outputs it, and an RF unit 312 that modulates the acceleration data output from the MCU 313 and transmits it by wireless way. The RF unit 312 is preferably a low-power FSK modulation device such as a Bluetooth (registered trademark). Note that another modulation method (SubGHz, Zigbee (registered trademark), WiFi etc.) can be used in the RF unit 312 as a matter of course.

A receiving unit 320 receives the acceleration data that is output from the transmitting unit 310, performs statistical processing on the acceleration data and thereby modifies a mounting error of the acceleration sensor. The receiving unit 320 is typically an information processing device such as a PC (personal computer), a server computer or a microcontroller. The receiving unit 320 includes an RF unit 322 that receives and demodulates the acceleration data that is transmitted by the RF unit 312, an MCU 323 that processes the acceleration data that is demodulated by the RF unit 322, and an action identification device 200 that receives the acceleration data that is output from the MCU 323 and performs action identification processing.

The action identification system 300 may further include a display unit 330 that displays an identification result by the action identification device 200 in a viewable manner.

Twelfth Embodiment

Figure 26:
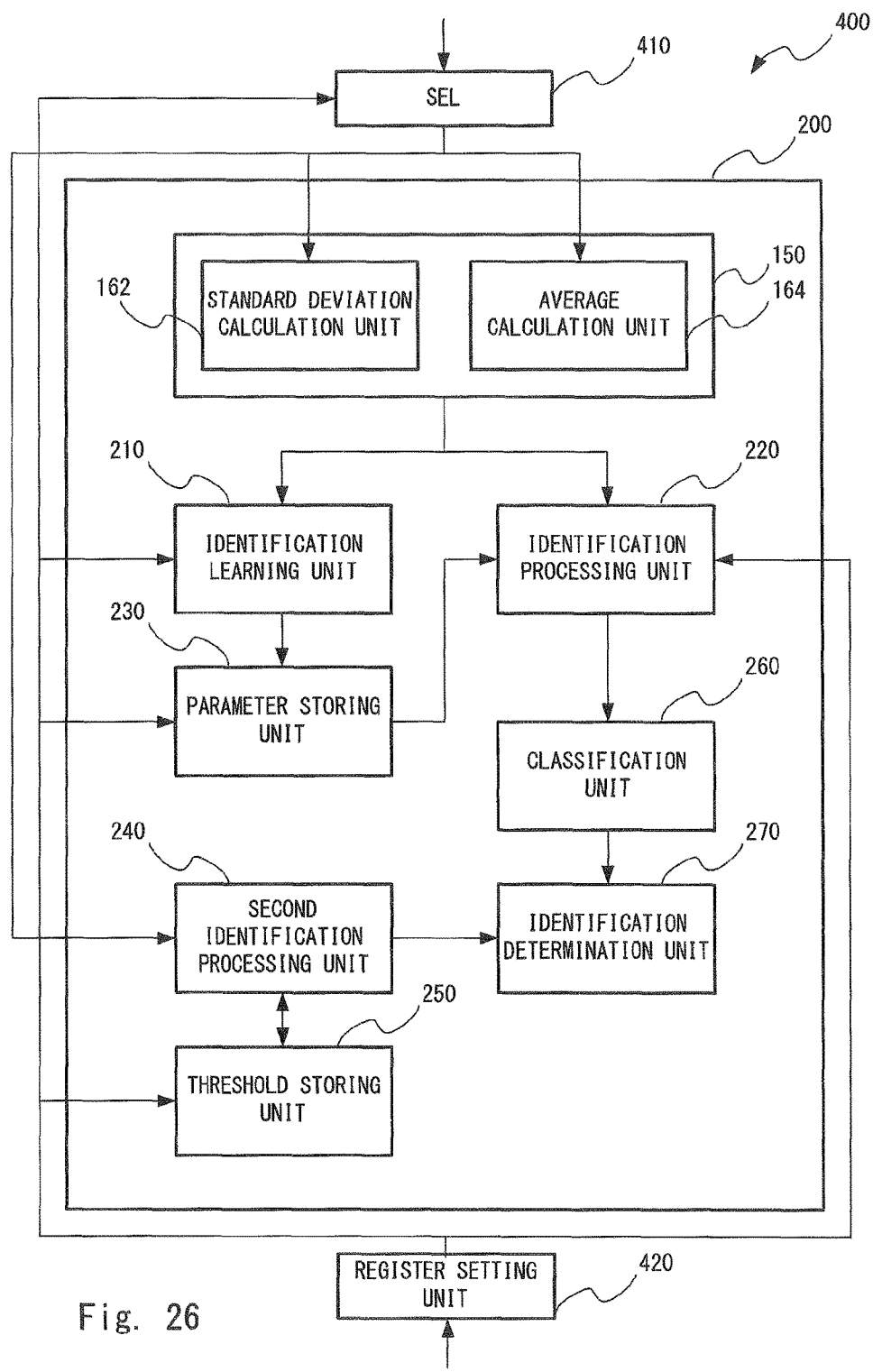
FIG. 26 is a view showing the configuration of a microcontroller 400 according to a twelfth embodiment.

A twelfth embodiment describes one example of a microcontroller 400 that includes an action identification device 200. FIG. 26 shows a configuration example of the microcontroller 400.

The microcontroller 400 includes an action identification device 200, a SEL 410, and a register setting unit 420.

The SEL 410 is a selector for selecting external input data and determining the transfer destination of the input data.

The register setting unit 420 performs control to switch the action identification device 200 to learning mode or identification mode according to external control. For example, it is the learning mode when a value of the register is set to 0, and it is the identification mode when a value of the register is set to 1.

When the register is set to 0, which is the learning mode, the register setting unit 420 controls the SEL 410 to select learning data as input data. Further, the register setting unit 420 sets the identification learning unit 210 to the operating state and sets the identification processing unit 220 to the suspended state.

After that, the standard deviation calculation unit 162 and the average calculation unit 164 of the phase correction device 150 and the second identification processing unit 240 start operating and calculate a feature quantity of the input data. Then, the input data that has been phase-corrected by the phase correction device 150 is input to the identification learning unit 210. The identification learning unit 210 calculates an action identification parameter and stores it into the parameter storing unit 230. Note that the identification parameter may be directly set from the outside through the register setting unit 420.

Concurrently, the second identification processing unit 240 stores an identification threshold into the threshold storing unit 250. The identification threshold may be also directly set from the outside through the register setting unit 420.

On the other hand, when the register is set to 1, which is the identification mode, the register setting unit 420 controls the SEL 410 to select identification data as input data. Further, the register setting unit 420 sets the identification learning unit 210 to the suspended state and sets the identification processing unit 220 to the operating state.

After that, the standard deviation calculation unit 162 and the average calculation unit 164 of the phase correction device 150 and the second identification processing unit 240 start operating and calculate a feature quantity of the input data. Then, the input data that has been phase-corrected by the phase correction device 150 is input to the identification processing unit 220.

The identification processing unit 220 performs action identification by using the identification parameter that is stored in the parameter storing unit 230. Concurrently, the second identification processing unit 240 performs action identification by using the identification threshold that is stored in the threshold storing unit 250.

Finally, the classification unit 260 makes classification into classes, and the identification determination unit 270 performs the final action identification and then ends the process.

Other Embodiments

Note that embodiments are not limited to the above-described embodiments and may be varied in many ways appropriately within the scope of the present invention. For example, the example that estimates a phase using a group of acceleration data whose standard deviation value is equal to or less than a threshold and performs phase correction on the same group of acceleration data is described in the eighth embodiment. However, it is feasible to perform phase correction on a group of acceleration data including data whose standard deviation value is not equal to or less than a threshold also using the above-described phase estimation result.

Further, the example in which the identification determination unit 270 performs highly accurate action identification by using an identification result of the second identification processing unit 240 is described in the ninth embodiment. However, the action identification device 200 does not necessarily have such a configuration, and it may simply output an identification result to be stored into the classification unit 260.

Further, although the example that performs a series of processing steps by using the average value of acceleration data for each certain time period is described in the above embodiments, an embodiment of the present invention is not limited thereto, and the same processing may be performed using another representative value. Note that, although acceleration data, not a representative value, can be used as it is for phase correction, learning and identification processing, this can cause an increase in processing load and a decrease in the accuracy of learning and identification.

Further, although each embodiment is implemented as a hardware configuration in the description of the above embodiments, the present invention is not limited thereto, and a given processing unit may be logically implemented by causing a CPU (Central Processing Unit) to execute a computer program. In this case, the computer program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

Further, the configurations of the above-described first to twelfth embodiments can be combined as desirable by one of ordinary skill in the art The whole or part of the embodiments disclosed above can be described as, but not limited to, the following supplementary notes.

(Supplementary Note 1)

A measurement device comprising:
an input unit that inputs a plurality of acceleration data; and
an analysis unit that compares a distribution of a first acceleration value based on the acceleration data with a distribution of a predetermined second acceleration value and thereby corrects the first acceleration value.

(Supplementary Note 2)

The measurement device according to Supplementary note 1, wherein the analysis unit corrects the first acceleration value according to a displacement between a slope of a straight line approximating the distribution of the first acceleration value and a slope of a straight line approximating the distribution of the second acceleration value.

(Supplementary Note 3)

The measurement device according to Supplementary note 1 or 2, wherein the analysis unit further corrects the first acceleration value according to a displacement between a center of a circular arc approximating the distribution of the first acceleration value and a center of a circular arc approximating the distribution of the second acceleration value.

(Supplementary Note 4)

The measurement device according to any one of Supplementary notes 1 to 3, wherein the first acceleration value is an average value of the acceleration data for each certain time period.

(Supplementary Note 5)

The measurement device according to any one of Supplementary notes 1 to 4, wherein the analysis unit stops acquisition of the acceleration data or correction of the first acceleration value based on the variation of a coefficient of determination for the acceleration data.

(Supplementary Note 6)

The measurement device according to any one of Supplementary notes 1 to 5, wherein the analysis unit generates and displays a graph representing at least one of the distribution of the first acceleration value and the distribution of the second acceleration value.

(Supplementary Note 7)

The measurement device according to any one of Supplementary notes 2 to 6, wherein the analysis unit performs approximation of the first acceleration value distributed in a specified data value region to the straight line.

(Supplementary Note 8)

The measurement device according to Supplementary note 1, wherein the input unit further receives input for classifying the acceleration data into a plurality of groups, and the analysis unit corrects, in each of the groups, the first acceleration value according to a displacement between the average value of the acceleration data classified into the group and a reference point predetermined for each of the groups.

(Supplementary Note 9)

The measurement device according to Supplementary note 1, wherein the analysis unit calculates, for each of a plurality of angles θ, a difference between an average value of acceleration data obtained by rotating the acceleration data by the angle θ and a predetermined reference value, and corrects the first acceleration value by using θ where the difference is smallest.

(Supplementary Note 10)

The measurement device according to any one of Supplementary notes 1 to 9, wherein the input unit repeatedly inputs the acceleration data at specified time intervals.

(Supplementary Note 11)

A measurement system comprising:

a sensor module that is mounted on an object under test and outputs acceleration data; and a measurement device that acquires the acceleration data from the sensor module, wherein the measurement device includes an input unit that inputs a plurality of acceleration data; and an analysis unit that compares a distribution of a first acceleration value based on the acceleration data with a distribution of a predetermined second acceleration value and thereby corrects the first acceleration value.

(Supplementary Note 12)

The measurement system according to Supplementary note 11, wherein the measurement device acquires the acceleration data from a plurality of sensor modules, and the analysis unit corrects the first acceleration value by using the acceleration data acquired from each of the sensor modules.

(Supplementary Note 13)

A measurement method comprising:

an input step of inputting a plurality of acceleration data; and an analysis step of comparing a distribution of a first acceleration value based on the acceleration data with a distribution of a predetermined second acceleration value and thereby correcting the first acceleration value.

(Supplementary Note 14)

A program causing a computer to execute the method according to Supplementary note 13.

While the invention has been described in terms of several embodiments, those skilled in the art will recognize that the invention can be practiced with various modifications within the spirit and scope of the appended claims and the invention is not limited to the examples described above.

Further, the scope of the claims is not limited by the embodiments described above.

Furthermore, it is noted that, Applicant's intent is to encompass equivalents of all claim elements, even if amended later during prosecution.

What is claimed is:

1. A phase correction device comprising:
a non-transitory computer readable medium storing computer instructions; and
a processor configured to execute the computer instructions to provide:
receiving a plurality of acceleration data and calculates a standard deviation of the plurality of acceleration data for each specified time period;
receiving the plurality of acceleration data and calculates a representative value of the acceleration data for each specified time period;
estimating a phase of the representative value in a space having a first coordinate axis and a second coordinate axis by using the representative value when the standard deviation is smaller than a specified threshold; and
performing phase correction of the representative value by using the estimated phase,
wherein the acceleration data is outputted by an acceleration sensor.

2. The phase correction device according to claim 1, wherein the estimating of the phase of the representative value performs at least one processing selected from:
processing that calculates a first phase based on an average of the representative values on a negative side of the first coordinate axis,
processing that calculates a second phase based on an average of the representative values on a positive side of the first coordinate axis, and
processing that estimates the phase based on the first phase and the second phase.

3. The phase correction device according to claim 2, wherein the estimating of the phase of the representative value further calculates a bias based on an average of the representative values near the second coordinate axis, calculates the first phase based on the bias and the average of the representative values on the negative side of the first coordinate axis, and calculates the second phase based on the bias and the average of the representative values on the positive side of the first coordinate axis.

4. The phase correction device according to claim 1, wherein the representative value is an average value, and
wherein the acceleration data is outputted by the acceleration sensor to the phase correction device.

5. The phase correction device according to claim 1, wherein the estimating of the phase the representative value updates a coordinate value of the second coordinate axis by an absolute value of the coordinate value of the second coordinate axis among the representative values.

6. An action identification device comprising:
the phase correction device according to claim 1;
wherein the processor is configured to execute the computer instructions to provide:
performing machine learning by using the representative value after phase correction by the phase correction device; and performing action identification by using the representative value after phase correction by the phase correction device.

7. The action identification device according to claim 6, further comprising:
wherein the processor is configured to execute the computer instructions to provide:
performing action identification without machine learning by using a feature quantity of the acceleration data; and
putting together action identification results by the identification processing unit and the second identification processing unit.

8. An action identification system comprising:
the action identification device according to claim 6; and
a transmitter including the acceleration sensor that is mounted on an object and outputs the acceleration data.

9. A microcontroller comprising:
the action identification device according to claim 6; and
a register setting hardware configured to set a value to a register to set any one of the performing action identification and the putting together of action identification to an operating state according to external control.

10. A phase correction method for a phase correction device, the method comprising:
a standard deviation calculation step of receiving a plurality of acceleration data and calculating a standard deviation of the plurality of acceleration data for each specified time period;
a representative value calculation step of receiving the plurality of acceleration data and calculating a representative value of the acceleration data for each specified time period;
a phase estimation step of estimating a phase of the representative value in a space having a first coordinate axis and a second coordinate axis by using the representative value when the standard deviation is smaller than a specified threshold; and
a phase correction step of performing phase correction of the representative value by using the estimated phase,
wherein the acceleration data is outputted by an acceleration sensor.

11. A non-transitory computer-readable recording medium storing a program causing a computer to execute the phase correction method according to claim 10.

12. A phase correction device comprising:
a standard deviation calculation circuit that receives a plurality of acceleration data and calculates a standard deviation of the plurality of acceleration data for each specified time period;
a representative value calculation circuit that receives the plurality of acceleration data and calculates a representative value of the acceleration data for each specified time period;
a phase estimation circuit that estimates a phase of the representative value in a space including a first coordinate axis and a second coordinate axis by using the representative value when the standard deviation is less than a specified threshold; and
a phase correction circuit that performs phase correction of the representative value by using the estimated phase,
wherein the acceleration data is outputted by an acceleration sensor.

13. The phase correction device according to claim 12, wherein the phase estimation circuit performs at least one processing selected from:
processing that calculates a first phase based on an average of the representative values on a negative side of the first coordinate axis,
processing that calculates a second phase based on an average of the representative values on a positive side of the first coordinate axis, and
processing that estimates the phase based on the first phase and the second phase.

14. The phase correction device according to claim 13, wherein the phase estimation circuit further calculates a bias based on an average of the representative values near the second coordinate axis, calculates the first phase based on the bias and the average of the representative values on the negative side of the first coordinate axis, and calculates the second phase based on the bias and the average of the representative values on the positive side of the first coordinate axis.

15. The phase correction device according to claim 12, wherein the representative value is an average value.

16. The phase correction device according to claim 12, wherein the phase correction circuit updates a coordinate value of the second coordinate axis by an absolute value of the coordinate value of the second coordinate axis among the representative values.

17. An action identification device comprising:
the phase correction device according to claim 12;
an identification learning circuit that performs machine learning by using the representative value after phase correction by the phase correction device; and
an identification processing circuit that performs action identification by using the representative value after phase correction by the phase correction device.

18. The action identification device according to claim 17, further comprising:
a second identification processing circuit that performs action identification without machine learning by using a feature quantity of the acceleration data; and
an identification determination circuit that puts together action identification results by the identification processing circuit and the second identification processing circuit.

19. An action identification system comprising:
the action identification device according to claim 17; and
a transmitter including the acceleration sensor that is mounted on an object and outputs the acceleration data.

20. A microcontroller comprising:
the action identification device according to claim 17; and
register setting circuit that sets any one of the identification learning circuit and the identification processing circuit to an operating state according to external control.

* * * * *